(12) United States Patent
Chi et al.

(10) Patent No.: US 7,868,170 B2
(45) Date of Patent: Jan. 11, 2011

(54) PLATINUM COMPLEX AND ORGANIC LIGHT-EMITTING DEVICE USING THE SAME

(75) Inventors: Yun Chi, Department of Chemistry, National Tsing Hua University, 101, Sec. 2, Kuang Fu Rd., Hsinchu (TW) 300; Pi-Tai Chou, Taipei (TW); Sheng-Yuan Chang, Hsinchu (TW)

(73) Assignee: Yun Chi (TW)

( * ) Notice: Subject to any disclaimer, the term of this patent is extended or adjusted under 35 U.S.C. 154(b) by 513 days.

(21) Appl. No.: 12/003,532

(22) Filed: Dec. 28, 2007

(65) Prior Publication Data

US 2009/0171087 A1    Jul. 2, 2009

(51) Int. Cl.
*C07F 15/00* (2006.01)
*H05B 33/10* (2006.01)

(52) U.S. Cl. .................. 546/10; 313/504; 428/690; 546/2; 546/5

(58) Field of Classification Search .................. 546/10, 546/5, 2; 428/690; 313/504
See application file for complete search history.

(56) References Cited

PUBLICATIONS

Chang, S. et al.: Luminescent Platinum complexes containing isoquinolinyl indazolate ligands: Synthetic pathways and photophysical properties. Inorg. Chem. vol. 46, pp. 7064-7074, 2007.*

Chang, S. et al.: Blue-Emitting Platinum complexes bearing both pyridylpyrazolate chelate and bridging pyrazolate ligands: Synthesis, structures, and photophysical properties. Inorg. Chem., published on web on Nov. 21, 2007.*

* cited by examiner

*Primary Examiner*—Charanjit S Aulakh
(74) *Attorney, Agent, or Firm*—Bacon & Thomas PLLC

(57) ABSTRACT

The present invention relates to a platinum complex as the following formula (I):

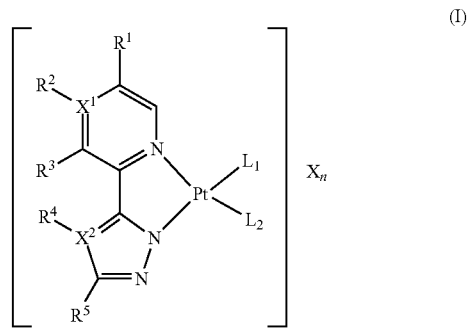

wherein X, n, $R^1$, $R^2$, $R^3$, $R^4$, $R^5$, $X^1$, $X^2$, $L^1$, and $L^2$ are defined the same as the specification. The present invention also further provides an organic light-emitting device using the same. The complexes of the present invention exhibit enhanced emission quantum yields, and short phosphorescence radiative lifetimes in the range of several microseconds so as to be applied in high efficiency OLEDs.

25 Claims, 10 Drawing Sheets

PLATINUM COMPLEX AND ORGANIC LIGHT-EMITTING DEVICE USING THE SAME

BACKGROUND OF THE INVENTION

1. Field of the Invention

The present invention relates to a platinum complex and an organic light-emitting device using the same and, more particularly, to a phosphorescent platinum complex and a phosphorescent organic light-emitting device using the same.

2. Description of Related Art

In general, the term "organic light-emitting phenomenon" refers to a phenomenon in which electric energy is converted to light energy by means of an organic material. The organic light-emitting device using the organic light-emitting phenomenon has a structure usually comprising an anode, a cathode and organic material layers interposed therebetween. Herein, the organic material layers may be mostly formed in a multilayer structure comprising layers of different materials, and contain an organic emissive layer that emits light by fluorescence or phosphorescence. An OLED generally comprises an anode, a hole source, an emissive layer (EML), an electron source and a cathode. The hole source may comprise a hole injection layer (HIL) and a hole transport layer (HTL). The electron source generally comprises an electron transport layer (ETL) and possibly an electron injection layer (EIL). Some OLEDs also comprise a thin layer of LiF between the electron source and the cathode. As shown in FIG. 1, there is shown a schematic representation of a typical OLED, comprising a substrate 100 and an anode 101, a hole transport layer 102, a hole injection layer 103, an emissive layer 104, an electron injection layer 105, an electron transport layer 106, a LiF thin layer 107 and a cathode 108 on the surface of the substrate 100 in sequence.

The emissive layer (EML), comprised of a host material doped with one or more luminescent materials, provides the function of light emission produced by excitons. The excitons are formed as a result of recombination of holes and electrons in the layer.

OLEDs are classified roughly into two types by a difference of mechanism of emission, namely the fluorescent OLED or phosphorescent OLED. It is well known that the phosphorescent OLED is advantageous from an aspect of emission quantum efficiency.

Owing to their potential to harness the energies of both the singlet and triplet excitons after charge recombination, transition metal based phosphorescent materials have recently received considerable attention in fabricating phosphorescent OLEDs. The main advantages are due to the heavy atom induced singlet-to-triplet intersystem crossing as well as the large enhancement of radiative decay rate from the resulting triplet manifolds. In this regard, numerous attempts have been made to exploit third-row transition metal complexes as dopant emitters for OLED fabrication, among which quite a few Pt(II), Os(II) and Ir(III) complexes have been reported to exhibit highly efficient device performances. Despite these developments, attempts to further expand the potential of the square planar Pt(II) complexes, in which the central metal ion possesses a higher atomic number than Os(II) and Ir(III) for efficient OLED applications, has encountered many intrinsic obstacles. For example, the PtOEP ($H_2$OEP=octaethylporphyrin) type of emitter commonly has a ligand based phosphorescence with lifetimes as long as 30~50 μs, so that saturation of emissive sites and a rapid drop in device efficiency at high drive current is observed. Also contributing to the poor device efficiency is the planar molecular configuration of many Pt(II) complexes, which leads to a stacking effect and hence the formation of aggregates or dimers that tend to form excimers in the electronically excited state.

In addition, as a light source for illumination or backlight, a white light is usually required. To realize a white OLED device, plural light emissive materials such as blue, green, red are used generally. However, blue phosphorescent materials have been the most difficult to prepare.

SUMMARY OF THE INVENTION

The object of the present invention is to reduce the phosphorescence radiative lifetime and prevent stacking behavior of platinum complexes so as to enhance the potential of platinum complexes for the application in high efficiency OLEDs.

To achieve the object, the present invention provides a platinum complex of the following formula (I):

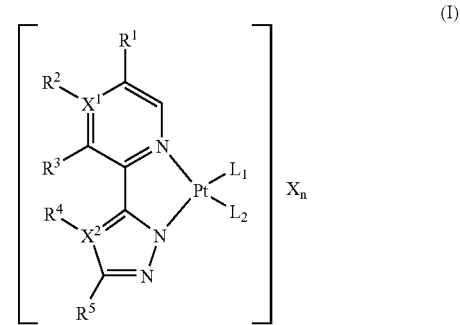

wherein

X is a counter ion;

n is 0 or 1;

$X^1$ and $X^2$ independently are C or N;

$R^1$, $R^2$ and $R^3$ independently are H, C1-C8 alkyl, phenyl, or C1-C4 perfluoroalkyl, $R^1$ is H and $R^2$ and $R^3$ together are

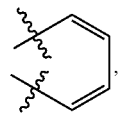

or $R^3$ is H and $R^1$ and $R^2$ together are

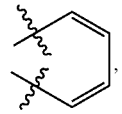

when $X^1$ is C;

$R^1$ and $R^3$ independently are H, C1-C8 alkyl, phenyl, or C1-C4 perfluoroalkyl and $R^2$ is omitted, when $X^1$ is N;

$R^4$ is H and $R^5$ is H, C1-C8 alkyl, phenyl, or C1-C4 perfluoroalkyl, or $R^4$ and $R^5$ together are C4-C8 alkylene or bridged carbocyclic C4-C12 alkylene, when $X^2$ is C;

$R^4$ is omitted and $R^5$ is H, C1-C8 alkyl, phenyl, or C1-C4 perfluoroalkyl, when $X^2$ is N; and $L^1$ and $L^2$ each are

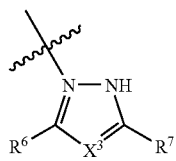

when n is 1, or together are

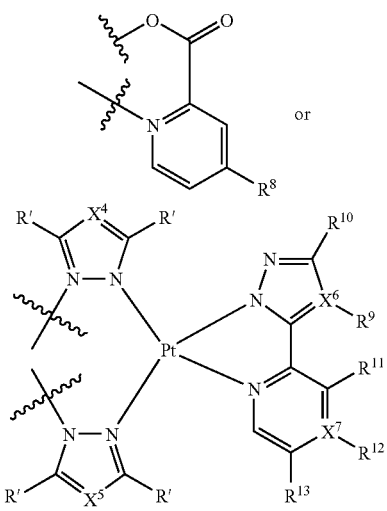

when n is 0, wherein $X^3$ is C or N; $R^6$ and $R^7$ independently are H, C1-C8 alkyl, phenyl, or C1-C4 perfluoroalkyl; $R^8$ is H, C1-C8 alkyl, phenyl, or C1-C4 perfluoroalkyl; $X^4$ and $X^5$ independently are C or N; each R' independently is H, C1-C8 alkyl, phenyl, or C1-C4 perfluoroalkyl; $X^6$ and $X^7$ independently are C or N; $R^9$ is H and $R^{10}$ is H, C1-C8 alkyl, phenyl, or C1-C4 perfluoroalkyl, or $R^9$ and $R^{10}$ together are C4-C8 alkylene or bridged carbocyclic C4-C12 alkylene, when $X^6$ is C; $R^9$ is omitted and $R^{10}$ is H, C1-C8 alkyl, phenyl, or C1-C4 perfluoroalkyl, when $X^6$ is N; $R^{11}$, $R^{12}$ and $R^{13}$ independently are H, C1-C8 alkyl, phenyl, or C1-C4 perfluoroalkyl, $R^{11}$ is H and $R^{12}$ and $R^{13}$ together are

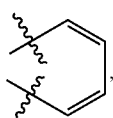

or $R^{13}$ is H and $R^{11}$ and $R^{12}$ together are

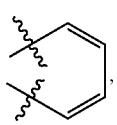

when $X^7$ is C; and $R^{11}$ and $R^{13}$ independently are H, C1-C8 alkyl, phenyl, or C1-C4 perfluoroalkyl and $R^{12}$ is omitted, when $X^7$ is N.

In the platinum complex of the formula (I) according to the present invention, X can be any free halogen ion, such as chloride ion.

In the platinum complex of the formula (I) according to the present invention, preferably, $R^4$ is H and $R^5$ is H, C1-C8 alkyl, phenyl, or C1-C4 perfluoroalkyl, or $R^4$ and $R^5$ together are

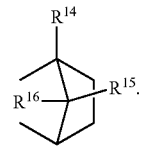

Herein, $R^{14}$, $R^{15}$, and $R^{16}$ independently are C1-8 alkyl.

In the platinum complex of the formula (I) according to the present invention, preferably, $R^9$ is H and $R^{10}$ is H, C1-C8 alkyl, phenyl, or C1-C4 perfluoroalkyl, or $R^9$ and $R^{10}$ together are

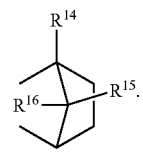

Herein, $R^{14}$, $R^{15}$, and $R^{16}$ are defined as above.

In the platinum complex of the formula (I) according to the present invention, preferably, $R^1$, $R^2$ and $R^3$ independently are H, C1-C8 alkyl, phenyl, or C1-C4 perfluoroalkyl while $R^4$ is H and $R^5$ is H, C1-C8 alkyl, phenyl, or C1-C4 perfluoroalkyl; or $R^1$ is H and $R^2$ and $R^3$ together are

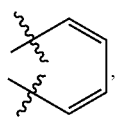

or $R^3$ is H and $R^1$ and $R^2$ together are

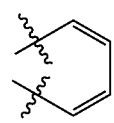

while $R^4$ and $R^5$ together are

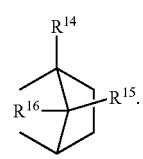

Herein, $R^{14}$, $R^{15}$, and $R^{16}$ are defined as above.

In the platinum complex of the formula (I) according to the present invention, preferably, $R^{11}$, $R^{12}$ and $R^{13}$ independently are H, C1-C8 alkyl, phenyl, or C1-C4 perfluoroalkyl while $R^9$ is H and $R^{10}$ is H, C1-C8 alkyl, phenyl, or C1-C4 perfluoroalkyl; or $R^{11}$ is H and $R^{12}$ and $R^{13}$ together are

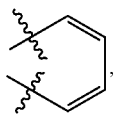

or $R^{13}$ is H and $R^{11}$ and $R^{12}$ together are

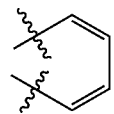

while $R^9$ and $R^{10}$ together are

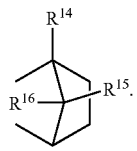

Herein, $R^{14}$, $R^{15}$, and $R^{16}$ are defined as above.

In the platinum complex of the formula (I) according to the present invention, more preferably, $X^1$, $X^2$, $X^3$, $X^4$, $X^5$, $X^6$ and $X^7$ each are C; $R^1$, $R^2$ and $R^3$ independently are H or C1-8 alkyl, $R^1$ is H and $R^2$ and $R^3$ together are

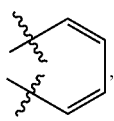

or $R^3$ is H and $R^1$ and $R^2$ together are

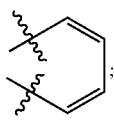

$R^4$ is H and $R^5$ is C1-C4 perfluoroalkyl, or $R^4$ and $R^5$ together are

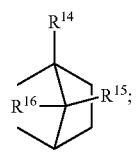

$R^6$ and $R^7$ each are H or C1-C8 alkyl; $R^8$ is H or C1-8 alkyl; each R' independently is H or C1-C8 alkyl; $R^9$ is H and $R^{10}$ is C1-C4 perfluoroalkyl, or $R^9$ and $R^{10}$ together are

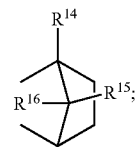

$R^{11}$, $R^{12}$ and $R^{13}$ independently are H or C1-8 alkyl, $R^{11}$ is H and $R^{12}$ and $R^{13}$ together are

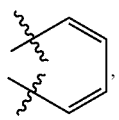

or $R^{13}$ is H and $R^{11}$ and $R^{12}$ together are

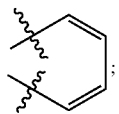

and $R^{14}$, $R^{15}$ and $R^{16}$ are C1-C8 alkyl.

In the platinum complex of the formula (I) according to the present invention, the associated ligand chromophores possess a bulky, rigid architecture to effectively suppress the aggregation effect. Furthermore, drastic reduction of the phosphorescence radiative lifetime to several microseconds has been achieved due to the strong singlet-triplet state mixings.

Specific examples of the platinum complex of the formula (I) according to the present invention are shown as follows, but are not limited thereto.

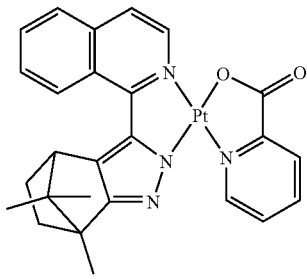

(I-1)

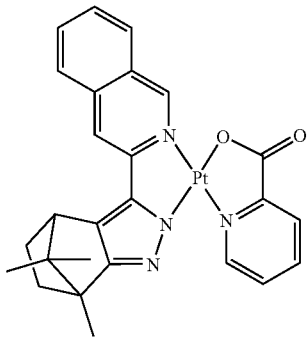

(I-2)

-continued

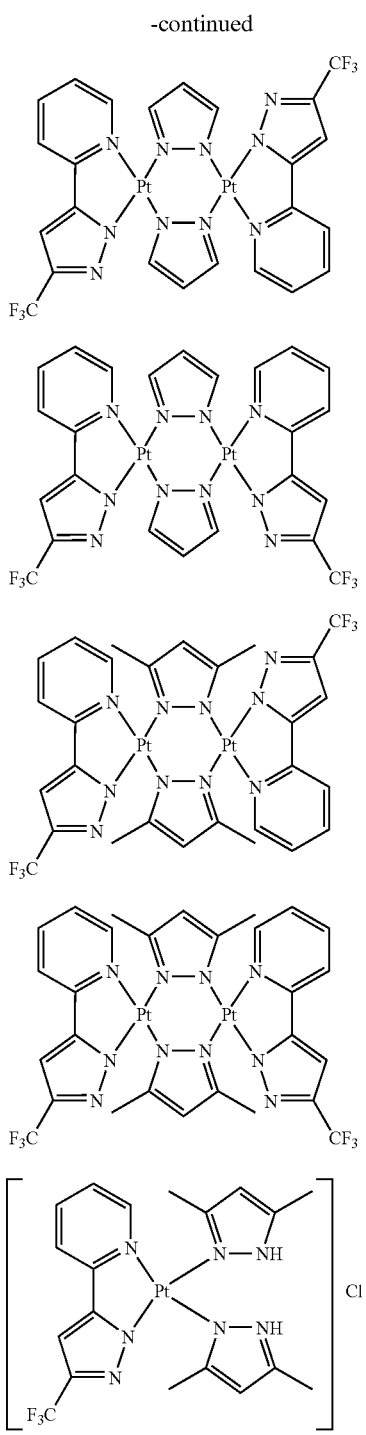

According to the photophysical measurements, the platinum complexes (I-1) to (I-7) exhibits improved quantum yield and reduced phosphorescence radiative lifetime so as to be applied in a high efficiency OLED. In addition, the platinum complexes (I-3) to (I-7) can emit blue light so as to function as blue phosphorescent materials which have been the most difficult to prepare.

Based on the aforementioned properties, the platinum complex of the formula (I) according to the present invention can be employed in an organic light-emitting device (OLED).

The organic light-emitting device may be the structure that comprises an anode, a cathode and one or more organic material layers including an emissive layer disposed between the electrodes.

Accordingly, the present invention further provides an organic light-emitting device, comprising: an anode; a cathode; and one or more organic material layers including an emissive layer disposed between the anode and the cathode, wherein at least one layer of the organic material layers comprises the platinum complex of the formula (I).

In the organic light-emitting device of the present invention, the organic material layers may be formed in a multilayer structure comprising a hole transport layer (HTL), an emissive layer (EML) and an electron transport layer (ETL).

In a phosphorescent OLED, a hole blocking layer is often used for the enhancement of luminance efficiency. Thereby, the OLED of the present invention can further comprise a hole blocking layer disposed between the electron transport and the emissive layer. In addition, the OLED of the present invention also can further comprise a LiF layer between the electron transport layer and the cathode.

The material of the anode is preferably a material having a large work function to facilitate hole injection usually to the organic material layers.

The material of the cathode is preferably a material having a small work function to facilitate electron injection usually to the organic material layers.

The material of the hole transport layer is a material having high hole mobility, which can transfer holes from the anode or the hole injection layer toward the emissive layer.

The material of the emissive layer is a material capable of emitting visible light by accepting and recombining holes from the hole transport layer and electrons from the electron transport layer, preferably a material having high quantum efficiency for fluorescence and phosphorescence.

The material of the electron transport layer is suitably a material having high electron mobility, which can easily receive electrons from the cathode and then transfer them to the emissive layer.

In the OLED of the present invention, it is preferable that the emissive layer comprises a host compound doped with the platinum complex of the formula (I) acting as a guest compound.

The organic light-emitting device according to the present invention may be of a front-sided, back-sided, or double-sided light emission according to the materials used.

The compound according to the present invention can also function in an organic electronic device including an organic solar cell, an organic photoconductor, and an organic transistor, according to a principle similar to that applied to the organic light-emitting device.

DETAILED DESCRIPTION OF THE PREFERRED EMBODIMENT

Figure 1:
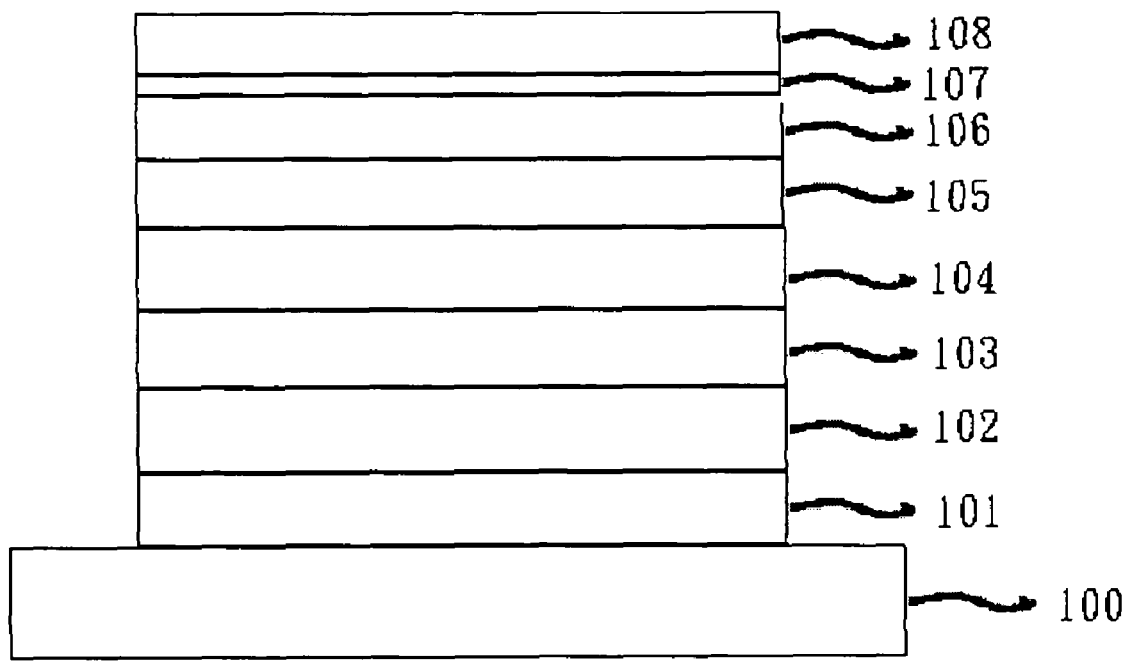
FIG. 1 shows a schematic representation of a typical OLED.
Figure 2:
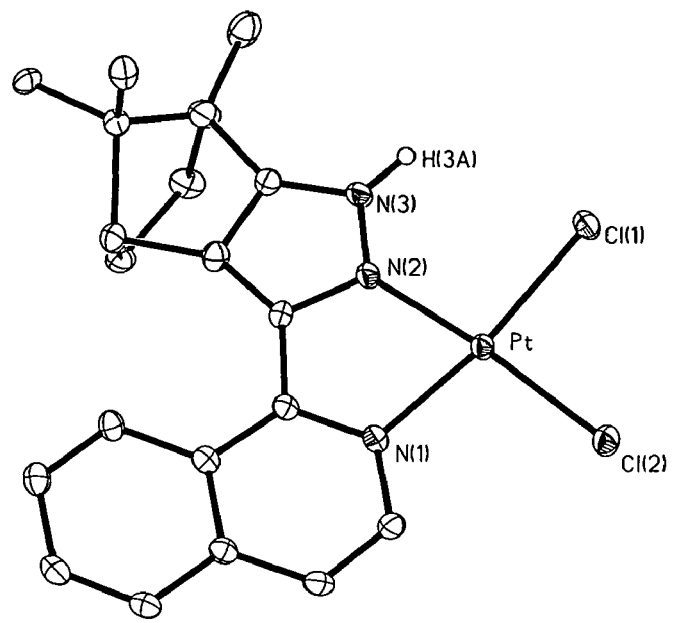
FIG. 2 shows the X-ray structure of Pt(1-iqdzH)Cl$_2$ synthesized in Synthesis Example 1 according to the present invention.
Figure 3:
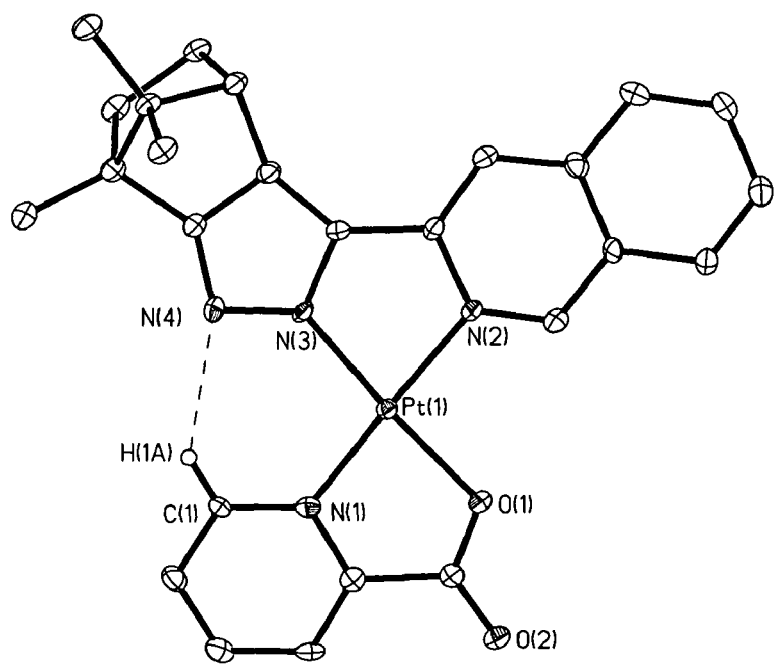
FIG. 3 shows the X-ray structure of Pt complex (I-2) synthesized in Synthesis Example 2 according to the present invention.
Figure 4:
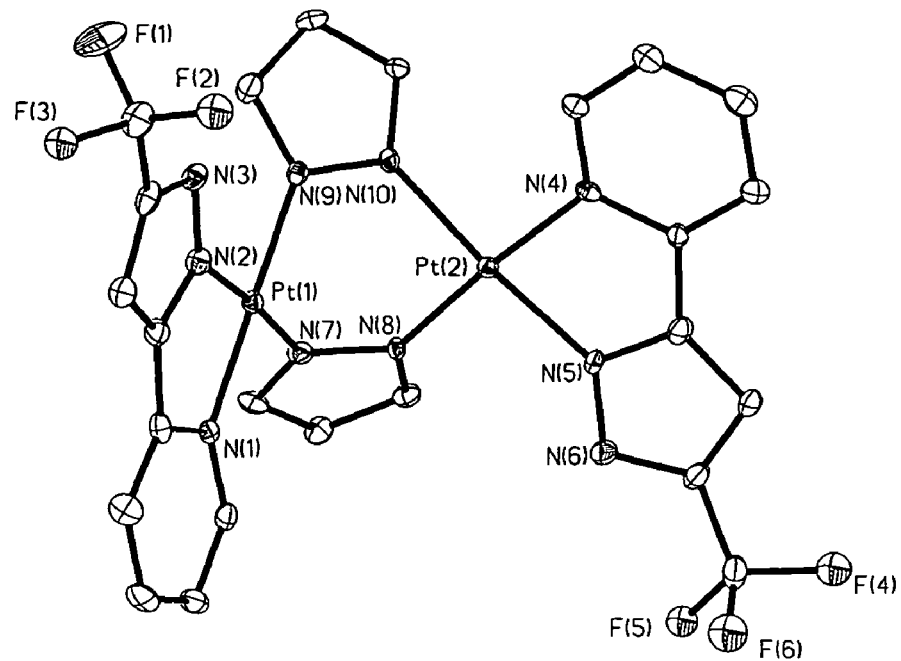
FIG. 4 shows the X-ray structure of Pt complex (I-3) synthesized in Synthesis Example 3 according to the present invention.
Figure 5:
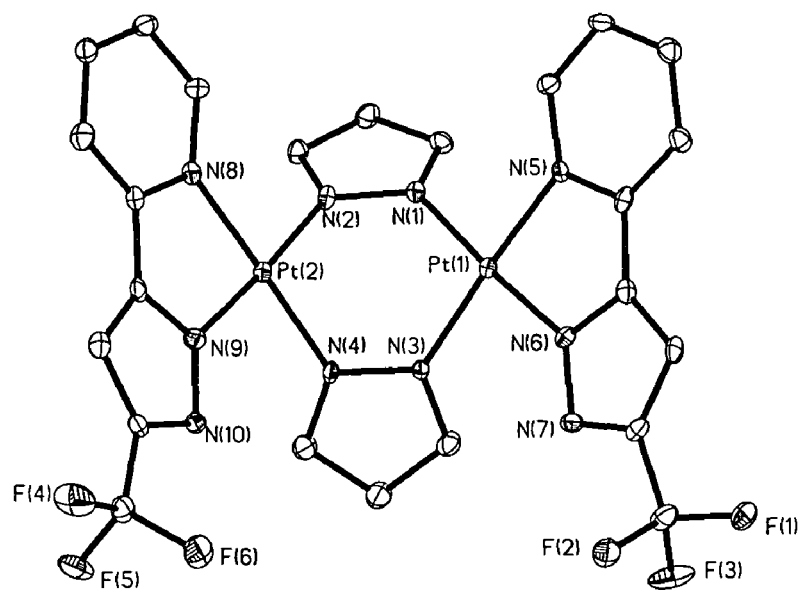
FIG. 5 shows the X-ray structure of Pt complex (I-4) synthesized in Synthesis Example 3 according to the present invention.
Figure 6:
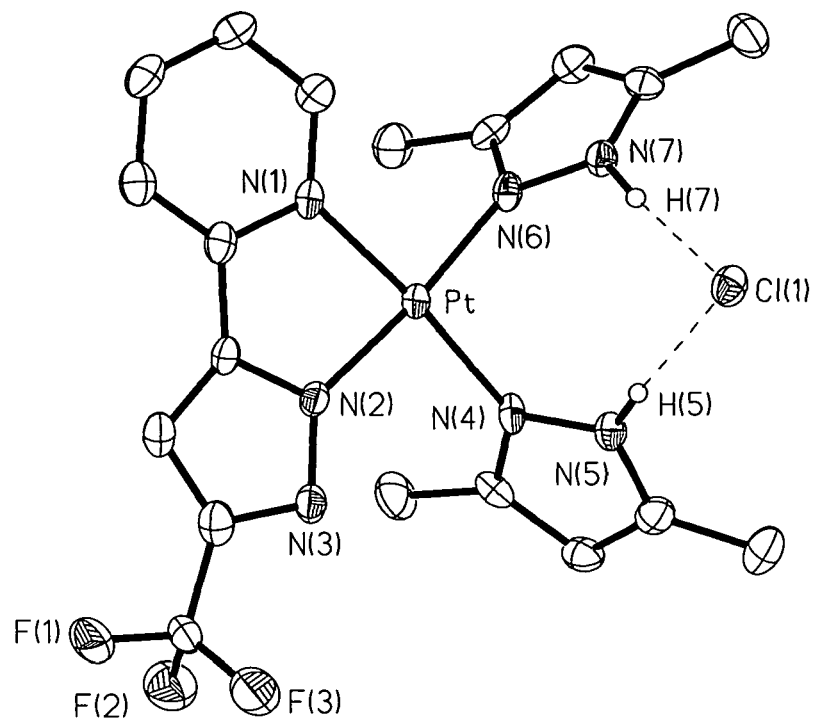
FIG. 6 shows the X-ray structure of Pt complex (I-7) synthesized in Synthesis Example 5 according to the present invention.

Hereinafter, preferable Examples are provided for the purpose of making the present invention more understandable. As such, Examples are provided for illustrating the invention, but the scope of the invention is not limited thereto.

(A) Synthesis

General procedures: All reactions were performed under nitrogen. Solvents were distilled from appropriate drying agents prior to use. Commercially available reagents were used without further purification unless otherwise stated. All reactions were monitored by TLC with Merck pre-coated glass plates (0.20 mm with fluorescent indicator UV$_{254}$). Compounds were visualized with UV light irradiation at 254 nm and 365 nm. Flash column chromatography was carried out using silica gel from Merck (230-400 mesh). Mass spectra were obtained on a JEOL SX-102A instrument operating in electron impact (EI) or fast atom bombardment (FAB) mode. $^1$H and $^{13}$C NMR spectra were recorded on a Bruker-400 or INOVA-500 instrument; chemical shifts are quoted with respect to the internal standard tetramethylsilane for $^1$H and $^{13}$C NMR data. Elemental analysis was carried out with a Heraeus CHN-O Rapid Elementary Analyzer.

X-ray structural analysis: Single crystal X-ray diffraction data were measured on a Bruker Smart CCD diffractometer using (Mo-K$_\alpha$) radiation ($\lambda$=0.71073 Å). The data collection was executed using the SMART program. Cell refinement and data reduction were made with the SAINT program. The structure was determined using the SHELXTL/PC program and refined using full-matrix least squares. Non-hydrogen atoms were refined anisotropically, whereas hydrogen atoms were placed at the calculated positions and included in the final stage of refinements with fixed parameters.

SYNTHESIS EXAMPLE 1

Synthesis of Platinum Complex (I-1)

A solution of potassium tetrachloroplatinate (K$_2$PtCl$_4$) (200 mg, 0.48 mmol), 4,8,8-Trimethyl-3-isoquinoline-1-yl-4,5,6,7-tetrahydro-2H-4,7-methano-indazole (1-iqdzH, 146 mg, 0.48 mmol) in H$_2$O (15 mL) and 4M HCl (1 mL) was heated to reflux for about 2 hours. After this period, the reaction mixture was cooled and the precipitated solid was filtered off, washed with ether and methanol and dried under vacuum to give Pt(1-iqdzH)Cl$_2$ as orange solid (171 mg, 63%).

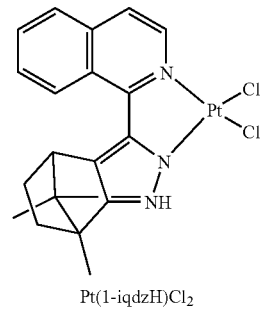

Pt(1-iqdzH)Cl$_2$

Spectral data of Pt(1-iqdzH)Cl$_2$: MS (FAB, $^{195}$Pt): m/z 569 (M)$^+$. $^1$H NMR (400 MHz, CDCl$_3$, 298K): δ 11.85 (s, 1H), 9.36 (d, J$_{HH}$=6.8 Hz, 1H), 8.58 (d, J$_{HH}$=8.4 Hz, 1H), 7.91 (d, J$_{HH}$=3.6 Hz, 2H), 7.79 (m, 1H), 7.64 (d, J$_{HH}$=6.8 Hz, 1H), 3.46 (d, J$_{HH}$=3.6 Hz, 1H), 2.34 (m, 1H), 2.03 (ddd, J$_{HH}$=12.3, 9.5, 2.9 Hz 1H), 1.56 (td, J$_{HH}$=10.7, 3.3 Hz, 1H), 1.47 (m, 1H), 1.43 (s, 3H), 1.05 (s, 3H), 0.84(s, 3H). Anal. Calcd. for C$_{20}$H$_{21}$Cl$_2$N$_3$Pt: C, 42.19; H, 3.72; N, 7.38. Found: C, 42.02; H, 4.03; N, 7.50.

X-ray: Crystals of Pt(1-iqdzH)Cl$_2$ suitable for X-ray analysis were obtained by recrystallization from a mixture of dichloromethane and hexane at room temperature.

Selected crystal data of Pt(1-iqdzH)Cl$_2$: C$_{20}$H$_{21}$Cl$_2$N$_3$Pt, M=569.39, Triclinic, space group P-1, a=8.1514(1), b=10.0314(2), c=12.0138(2) Å, α=81.8893(9)°, β=85.7748(11)°, γ=83.3597(10)°, V=964.37(3) Å$^3$, Z=2, ρ$_{calcd}$=1.961 Mgm$^{-3}$, F(000)=548, crystal size=0.25×0.14×0.10 mm$^3$, λ(Mo-K$_\alpha$)=0.7107 Å, T=150(2) K, μ=7.561 mm$^{-1}$, 15484 reflections collected (R$_{int}$=0.0586), final R$_1$[all data]=0.0356 and wR$_2$(all data)=0.0670.

Subsequently, a solution of [Pt(1-iqdzH)Cl$_2$] (100 mg, 0.18 mmol), picolinic acid (54 mg, 0.44 mmol) and Na$_2$CO$_3$ (186 mg, 1.75 mmol) in 2-methoxyethanol (30 mL) was heated at 100° C. for 16 hr. An excess of water was added after the solution was cooled to room temperature. The precipitate was filtered and dried under vacuum. Finally, this mixture was further purified by silica gel column chromatography (ethyl acetate and hexane=1:1) and recrystallized from CH$_2$Cl$_2$ and hexane to give orange [Pt(1-iqdz)(pic)] (compound (I-1), 41 mg, 38%) and red [Pt(1-iqdz)$_2$] (8 mg, 6%).

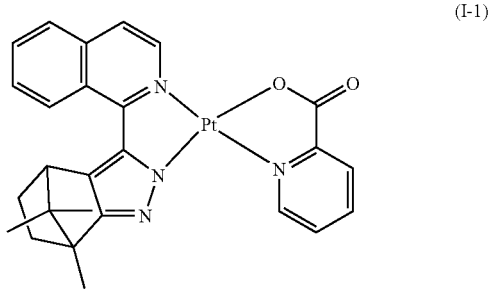

(I-1)

Spectral data of compound (I-1): MS (FAB, $^{195}$Pt): m/z 620 (M+1)$^+$.

$^1$H NMR (400 MHz, CDCl$_3$, 298 K): δ 10.50 (d, J$_{HH}$=6.2 Hz, 1H), 8.73 (m, 2H), 8.12 (dd, J$_{HH}$=8.0, 7.4 Hz, 1H), 8.03 (d, J$_{HH}$=7.6 Hz 1H), 7.85 (d, J$_{HH}$=8.0 Hz, 1H), 7.79 (dd, J$_{HH}$=7.6, 7.2 Hz, 1H), 7.71 (dd, J$_{HH}$=7.4, 6.2 Hz, 2H), 7.44 (d, J$_{HH}$=6.8 Hz, 1H), 3.34 (d, J$_{HH}$=4.0 Hz, 1H), 2.25 (m, 1H), 1.92 (m, 1H), 1.43 (s, 3H), 1.39 (m, 2H), 1.02 (s, 3H), 0.81 (s, 3H). Anal. Calcd. for C$_{26}$H$_{24}$N$_4$O$_2$Pt: C, 50.40; H, 3.90; N, 9.04. Found: C, 49.90; H, 4.09; N, 8.75.

SYNTHESIS EXAMPLE 2

Synthesis of Platinum Complex (I-2)

The same procedure was carried out as in Synthesis Example 1 except that 3-isoquinoline-3-yl-7,8,8-trimethyl-4,5,6,7-tetrahydro-2H-4,7-methano-indazole (3-iqdzH) was used instead of 4,8,8-Trimethyl-3-isoquinoline-1-yl-4,5,6,7-tetrahydro-2H-4,7-methano-indazole (1-iqdzH) and Pt(3-iqdzH)Cl$_2$ was used instead of Pt(1-iqdzH)Cl$_2$. The derivatives [Pt(3-iqdz)(pic)] (compound (I-2)) and [Pt(3-iqdz)$_2$] can be obtained in 44% and 4% yield.

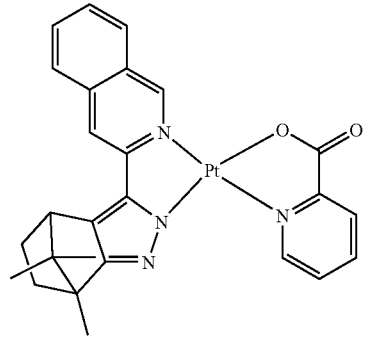

(I-2)

Spectral data of compound (I-2): MS (FAB, $^{195}$Pt): m/z 620 (M+1)$^+$.

$^1$H NMR (400 MHz, CDCl$_3$, 298 K): δ 10.51 (d, J$_{HH}$=5.6 Hz, 1H), 9.55 (s, 1H), 8.13 (dd, J$_{HH}$=8.0, 7.4 Hz, 1H), 8.03 (m, 2H), 7.81 (m, 3H), 7.73 (dd, J$_{HH}$=7.4, 5.6 Hz, 1H), 7.59 (dd, J$_{HH}$=8.0, 7.2 Hz, 1H), 3.13 (d, J$_{HH}$=3.2 Hz, 1H), 2.17 (m, 1H), 1.88 (m, 1H), 1.40 (s, 3H), 1.37 (m, 1H), 1.24 (m, 1H), 1.00 (s, 3H), 0.80 (s, 3H). Anal. Calcd. for C$_{26}$H$_{24}$N$_4$O$_2$Pt: C, 50.40; H, 3.90; N, 9.04. Found: C, 49.95; H, 4.07; N, 8.96.

X-ray: Crystals of compound (I-2) suitable for X-ray analysis were obtained by recrystallization from a mixture of dichloromethane and hexane at room temperature.

Selected crystal data of compound (I-2): C$_{26}$H$_{24}$N$_4$O$_2$Pt, M=619.58, Monoclinic, space group P2(1), a=10.4558(1), b=19.5010(2), c=10.8625(1) Å, α=90°, β=96.9912(8)°, γ=90°, V=2198.38(4) Å$^3$, Z=4, ρ$_{calcd}$=1.872 Mgm$^{-3}$, F(000)=1208, crystal size=0.25×0.20×0.18 mm$^3$, λ(Mo-K$_\alpha$)=0.7107 Å, T=150(2) K, μ=6.415 mm$^{-1}$, 19249 reflections collected (R$_{int}$=0.0369), final R$_1$[all data]=0.0277 and wR$_2$(all data)=0.0647.

SYNTHESIS EXAMPLE 3

Synthesis of Platinum Complexs (I-3) and (I-4)

A solution of potassium tetrachloroplatinate (K$_2$PtCl$_4$) (0.21 g, 0.5 mmol), 3-trifluoromethyl-5-(2-pyridyl)pyrazole (fppzH, 106 mg, 0.5 mmol) in a mixture of 4 M HCl (1 mL) and water (15 mL) was refluxed for about 2 hours. After this period, the reaction mixture was cooled and the precipitated solid was filtered off, washed with diethyl ether and hexane. Further purification was recrystallization from acetone, affording Pt(fppzH)(Cl)$_2$ as yellow solid 77% (0.19 g, 0.39 mmol).

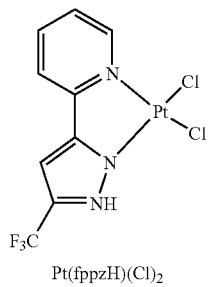

Pt(fppzH)(Cl)$_2$

Spectral data of Pt(fppzH)(Cl)$_2$: MS (FAB, $^{195}$Pt): m/z 479 (M$^+$), 443 (M$^+$-HCl). $^1$H NMR (400 MHz, d$_6$-acetone, 298

K): d 9.45 (d, $J_{HH}$=6.0 Hz, 1H), 8.38 (dd, $J_{HH}$=7.6, 7.2 Hz, 1H), 8.30 (d, $J_{HH}$=7.6 Hz, 1H), 7.88 (s, 1H), 7.77 (dd, $J_{HH}$=7.2, 6.0 Hz, 1H). $^{19}$F (470 MHz, $d_6$-acetone, 298 K): δ −61.12 (s, CF$_3$). Anal. Calcd. for C$_9$H$_6$Cl$_2$F$_3$N$_3$Pt: C, 22.56; H, 1.26; N, 8.77. Found: C, 22.37; H, 1.48; N, 8.59.

Subsequently, Pt(fppzH)Cl$_2$ (0.1 g, 0.21 mmol), pyrazole (36 mg, 0.52 mmol) and triethylamine (1 mL) in CH$_2$Cl$_2$ was stirred at room temperature for about 12 hours. After that, the product mixture was then washed with water, and concentrated to dryness under reduced pressure, giving pale-yellow powder. Further separation was by silica gel TLC plates (CH$_2$Cl$_2$). Trans-[(fppz)Pt(μ-pz)]$_2$ (compound (I-3)) was recrystallized from CH$_2$Cl$_2$ and cis-[(fppz)Pt(μ-pz)]$_2$ (compound (I-4)) was recrystallized from acetone, affording trans-[(fppz)Pt(μ-pz)]$_2$ as white solid 22% (compound (I-3), 0.022 g, 0.023 mmol) and cis-[(fppz)Pt(μ-pz)]$_2$ as white solid 45% (compound (I-4), 0.045 g, 0.047 mmol).

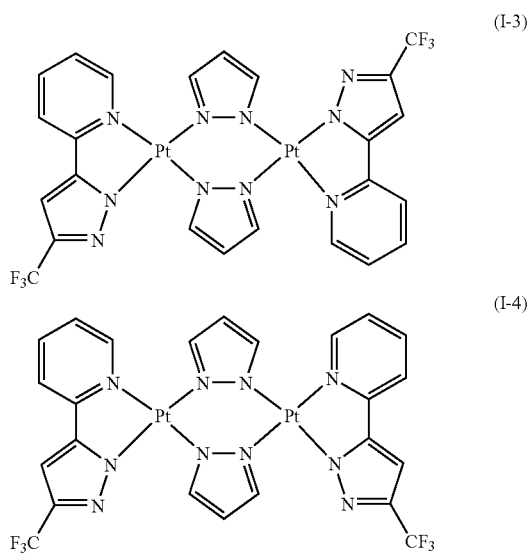

Spectral data of compound (I-3): MS (FAB, $^{195}$Pt): m/z 949 (M$^+$).

$^1$H NMR (400 MHz, $d_6$-acetone, 298 K): d 8.21 (ddd, $J_{HH}$=7.6, 7.4, 1.3 Hz, 2H), 8.13 (d, $J_{HH}$=6.0 Hz, 2H), 8.06 (d, $J_{HH}$=7.4 Hz, 2H), 7.96 (d, $J_{HH}$=2.4 Hz, 2H), 7.82 (d, $J_{HH}$=2.0 Hz, 2H), 7.47 (ddd, $J_{HH}$=7.6, 6.0, 1.3 Hz, 2H), 7.20 (s, 2H), 6.48 (dd, $J_{HH}$=2.4, 2.0 Hz, 2H). $^{19}$F (470 MHz, $d_6$-acetone, 298 K): δ −60.99 (s, CF$_3$). Anal. Calcd. for C$_{24}$H$_{16}$F$_6$N$_{10}$Pt$_2$: C, 30.39; H, 1.70; N, 14.77. Found: C, 30.27; H, 1.86; N, 14.68.

X-ray: Crystals of compound (I-3) suitable for X-ray analysis were obtained by recrystallization from dichloromethane at room temperature Selected crystal data of compound (I-3). CH$_2$Cl$_2$: C$_{25}$H$_{18}$Cl$_2$F$_6$N$_{10}$Pt$_2$, M=1033.57, Monoclinic, space group P2(1)/n, a=11.1587(6), b=21.3575(12), c=13.2677(7)Å, α=90°, β=108.591(1)°, γ=90°, V=2997.0(3) Å$^3$, Z=4, ρ$_{calcd}$=2.291 Mgm$^{-3}$, F(000)=1928, crystal size=0.16×0.08× 0.04 mm$^3$, λ(Mo-K$_α$)=0.7107 Å, T=150(2) K, μ=9.578 mm$^{-1}$, 22499 reflections collected (R$_{int}$=0.0603), final R$_1$[all data]=0.0557 and wR$_2$(all data)=0.0809.

Spectral data of compound (I-4): MS (FAB, $^{195}$Pt): m/z 949 (M$^+$).

$^1$H NMR (400 MHz, $d_6$-acetone, 298 K): d 8.33 (d, $J_{HH}$=6.0 Hz, 2H), 8.18 (dd, $J_{HH}$=7.8, 6.2 Hz, 2H), 8.04 (d, $J_{HH}$=7.8 Hz, 2H), 7.95 (d, $J_{HH}$=2.2 Hz, 2H), 7.86 (d, $J_{HH}$=2.4 Hz, 2H), 7.37 (dd, $J_{HH}$=6.2, 6.0 Hz, 2H), 7.13 (s, 2H), 6.60 (t, $J_{HH}$=2.2 Hz, 1H), 6.32 (t, $J_{HH}$=2.4 Hz, 1H). $^{19}$F (470 MHz, $d_6$-acetone, 298 K): δ −61.16 (s, CF$_3$). Anal. Calcd. for C$_{24}$H$_{16}$F$_6$N$_{10}$Pt$_2$: C, 30.39; H, 1.70; N, 14.77. Found: C, 30.22; H, 1.99; N, 14.58.

X-ray: Crystals of compound (I-4) suitable for X-ray analysis were obtained by recrystallization from acetone at room temperature.

Selected crystal data of compound (I-4). C$_3$H$_6$O: C$_{27}$H$_{22}$F$_6$N$_{10}$OPt$_2$, M=1006.73, Monoclinic, space group P2(1)/n, a=17.4642(10), b=8.6594(5), c=19.8926(11) Å, α=90°, β=103.6440(10)°, γ=90°, V=2923.5(3) Å$^3$, Z=4, ρ$_{calcd}$=2.287 Mgm$^{-3}$, F(000)=1888, crystal size=0.25×0.12× 0.05 mm$^3$, λ(Mo-K$_α$)=0.7107 Å, T=150(2) K, μ=9.641 mm$^{-1}$, 21992 reflections collected (R$_{int}$=0.0458), final R$_1$[all data]=0.0457 and wR$_2$(all data)=0.0895.

SYNTHESIS EXAMPLE 4

Synthesis of Platinum Complexes (I-5) and (I-6)

Pt(fppzH)(Cl)$_2$ was prepared by the same procedure as in Synthesis Example 3. Subsequently, Pt(fppzH)Cl$_2$ (0.1 g, 0.21 mmol), 3,5-dimethylpyrazole (dmpzH, 50 mg, 0.52 mmol) and triethylamine (1 mL) in CH$_2$Cl$_2$ was stirred at room temperature for about 12 hours. After that, the product mixture was then washed with water, and concentrated to dryness under reduced pressure, giving pale-yellow powder. Further separation was by silica gel TLC plates (CH$_2$Cl$_2$). Trans-[(fppz)Pt(μ-dmpz)]$_2$ (compound (I-5)) was recrystallized from acetone and cis-[(fppz)Pt(μ-dmpz)]$_2$ (compound (I-6)) was recrystallized from CH$_2$Cl$_2$, affording tran-[(fppz)Pt(μ-dmpz)]$_2$ as white solid 29% (compound (I-5), 0.03 g, 0.03 mmol) and cis-[(fppz)Pt(μ-dmpz)]$_2$ as white solid 41% (compound (I-6), 0.044 g, 0.044 mmol).

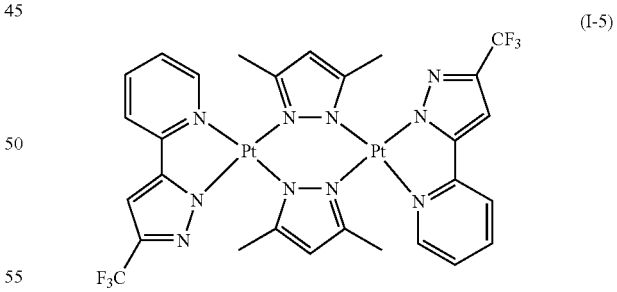

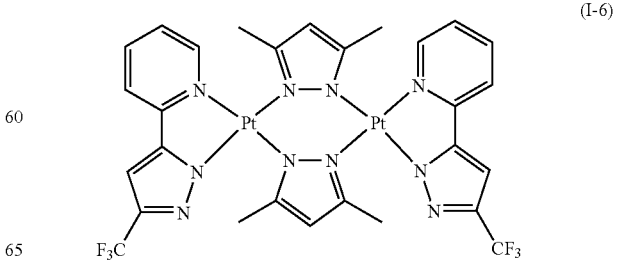

Spectral data of compound (I-5): MS (FAB, $^{195}$Pt): m/z 1004 (M$^+$).
$^1$H NMR (400 MHz, d$_6$-acetone, 298 K): δ 8.13 (dd, J$_{HH}$=8.2, 6.8 Hz, 2H), 8.05 (d, J$_{HH}$=6.0 Hz, 2H), 7.95 (d, J$_{HH}$=8.2 Hz, 2H), 7.39 (dd, J$_{HH}$=6.8, 6.0 Hz, 2H), 7.06 (s, 2H), 6.00 (s, 2H), 2.42 (s, 6H), 2.32 (s, 6H). $^{19}$F (470 MHz, d$_6$- acetone, 298 K): δ −61.07 (s, CF$_3$). Anal. Calcd. for C$_{28}$H$_{24}$F$_6$N$_{10}$Pt$_2$: C, 33.47; H, 2.41; N, 13.94. Found: C, 33.31; H, 2.58; N, 14.13.

Spectral data of compound (I-6): $^1$H NMR (400 MHz, d$_6$-DMSO, 298 K): δ 8.17 (dd, J$_{HH}$=7.8, 7.0 Hz, 2H), 8.09 (d, J$_{HH}$=6.2 Hz, 2H), 8.06 (d, J$_{HH}$=7.8 Hz, 2H), 7.35 (dd, J$_{HH}$=7.0, 6.2 Hz, 2H), 7.28 (s, 2H), 6.19 (s, 1H), 5.91 (s, 1H), 2.27 (br, 12H). $^{19}$F (470 MHz, d$_6$-DMSO, 298 K): δ −59.14 (s, CF$_3$). Anal. Calcd. for C$_{28}$H$_{24}$F$_6$N$_{10}$Pt$_2$: C, 33.47; H, 2.41; N. 13.94. Found: C, 33.29; H, 2.61; N, 14.10.

SYNTHESIS EXAMPLE 5

Synthesis of Platinum Complex (I-7)

[Pt(fppzH)Cl$_2$] was prepared by the same procedure as in Synthesis Example 3. Subsequently, [Pt(fppzH)Cl$_2$] (150 mg, 0.31 mmol) and 3,5-dimethylpyrazole (dmpzH, 75 mg, 0.78 mmol) in 30 mL of CH$_2$Cl$_2$ was stirred at room temperature for 12 hours. After then, the solution was washed with water and concentrated to dryness under reduced pressure. Further purification was conducted by repeated recrystallization from methanol solution, from which the less soluble yellow and the relatively more soluble pale-yellow crystalline solid were identified to be [Pt(fppz)(dmpzH)Cl] (20 mg, 0.04 mmol, 12%) and [Pt(fppz)(dmpzH)$_2$]Cl (compound (I-7), 100 mg, 0.16 mmol, 52%), respectively.

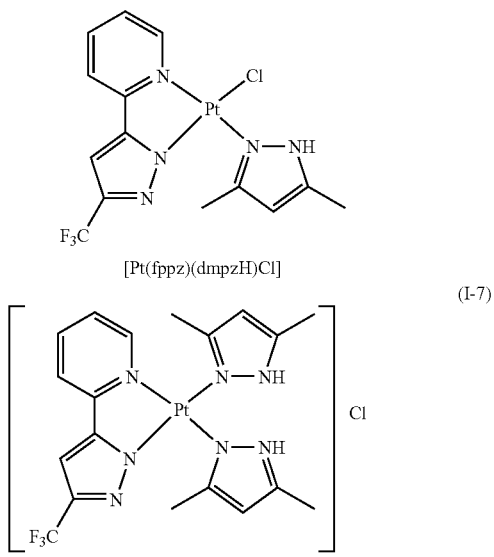

Spectral data of [Pt(fppz)(dmpzH)Cl]: MS (FAB, $^{195}$Pt): m/z 537 (M−1)$^+$. $^1$H NMR (400 MHz, CD$_2$Cl$_2$, 298 K): δ 12.21 (br, 1H), 8.76 (d, J$_{HH}$=6.5 Hz, 1H), 7.75 (t, J$_{HH}$=7.8, 7.2 Hz, 1H), 7.44 (d, J$_{HH}$=7.8 Hz, 1H), 6.87 (t, J$_{HH}$=7.2, 6.5 Hz, 1H), 6.84 (s, 1H), 5.94 (br, 1H), 2.41 (s, 3H), 2.15 (s, 3H). $^{19}$F NMR (470 MHz, CD$_2$Cl$_2$, 298 K): δ −61.32 (s, CF$_3$). Anal. Calcd. for C$_{14}$H$_{13}$ClF$_3$N$_5$Pt: C, 31.21; H, 2.43; N, 13.00. Found: C, 31.03; H, 2.60; N, 13.10.

Spectral data of compound (I-7): MS (FAB, $^{195}$Pt): m/z 599 (M−Cl)$^+$, 598 (M−HCl)$^+$. $^1$H NMR (400 MHz, CD$_2$Cl$_2$, 298 K): δ 15.13 (br, 1H), 14.53 (br, 1H), 7.97 (m, 1H), 7.74 (d, J$_{HH}$=7.6 Hz, 1H), 7.08 (m, 2H), 6.90 (s, 1H), 6.08 (br, 1H), 6.04 (br, 1H), 2.46 (br, 6H), 2.45 (s, 3H), 2.39 (s, 3H). $^{19}$F NMR (470 MHz, CD$_2$Cl$_2$, 298 K): δ −61.36 (s, CF$_3$). Anal. Calcd. for C$_{19}$H$_{21}$ClF$_3$N$_7$Pt: C,35.94; H, 3.33; N, 15.44. Found: C, 35.77; H, 3.60; N, 15.31.

X-ray: Crystals of compound (I-7) suitable for X-ray analysis were obtained by recrystallization from methanol at room temperature.

Selected crystal data of compound (I-7): Cl$_{19}$H$_{21}$ClF$_3$N$_7$Pt, M=634.97, Monoclinic, space group P2(1)/c, a=10.9312(10), b=20.0897(19), c=9.9253(10) Å, α=90°, β=98.352(2)°, γ=90°, V=2156.5(4) Å$^3$, Z=4, ρ$_{calcd}$=1.956 Mgm$^{−3}$, F(000)=1224, crystal size=0.42×0.30× 0.05 mm$^3$, λ(Mo-K$_α$)=0.7107 Å, T=150(2) K, μ=6.678 mm$^{−1}$, 16284 reflections collected (R$_{int}$=0.0594), final R$_1$[all data]=0.0344 and wR$_2$(all data)=0.0771.

(B) Spectroscopic and Dynamic Measurement

Steady-state absorption and emission spectra were recorded on a Hitachi (U-3310) spectrophotometer and an Edinburgh (FS920) fluorimeter, respectively. Both wavelength-dependent excitation and emission response of the fluorimeter were calibrated. A configuration of front-face excitation was used to measure the emission of the solid sample, in which the cell was made by assembling two edge-polished quartz plates with various Teflon spacers. A combination of appropriate filters was used to avoid interference from the scattering light. Lifetime studies were performed by an Edinburgh FL 900 photon-counting system with a hydrogen-filled/or a nitrogen lamp as the excitation source. Data were analyzed using a nonlinear least squares procedure in combination with an iterative convolution method. The emission decays were analyzed by the sum of exponential functions, which allows partial removal of the instrument time broadening and consequently renders a temporal resolution of ~200 ps.

To determine the photoluminescence quantum yield in solution, samples were degassed by three freeze-pump-thaw cycles under vigorous stirring conditions. 4-(Dicyanomethylene)-2-methyl-6-(p-dimethylamino styryl)-4H-pyran (DCM, λem=615 nm, Exciton, Inc.) in methanol was used as a reference, assuming a quantum yield of 0.43 with a 430 nm excitation. An integrating sphere (Labsphere) was applied to measure the quantum yield in the solid state, in which the solid sample film was prepared via direct vacuum deposition methods. The resulting luminescence was led to an intensified charge-coupled detector for subsequent quantum yield analyses. To obtain the PL quantum yield in solid state, the emission was collected via integrating sphere, and the quantum yield was calculated according to a reported method. [J. C. de Mello, H. F. Wittmann, R. H. Friend, *Adv. Mater.* 1997, 9, 230.]

The photophysical properties of platinum complexes (I-1) to (I-7) are shown in Table 1. The absorption spectra and the emission spectra thereof are shown in FIGS. 7-13.

TABLE 1

| Complex | $\lambda_{max(absorption)}$ ($\epsilon \times 10^3$, $M^{-1}cm^{-1}$) | $\lambda_{max(emission)}$ (nm) | Φ (%) | $\tau_{obs}$ (μs) | $k_r$ ($s^{-1}$) | $k_{nr}$ ($s^{-1}$) |
|---|---|---|---|---|---|---|
| I-1 | 329(7.7), 345(11.1), 372(8.7), 388(9.2), 450(2.5) | 587, 612 | 64 | 8.2 | $7.8 \times 10^4$ | $4.4 \times 10^4$ |
| I-2 | 326(23.0), 376(6.4), 434(2.0) | 567 | 3.5 | 0.85 | $4.1 \times 10^4$ | $1.1 \times 10^6$ |
| I-3 | 263(25.9), 316(22.4), 355(5.1) | (446, 476, 502); [445, 470, 500, 540] | (55) | (9.1); [20.9] | $(6.0 \times 10^4)$ | $(5.0 \times 10^4)$ |
| I-4 | 266(27.0), 318(23.9), 349(7.5) | (451, 478, 506); [440, 472, 500, 540] | (28) | (6.1); [20.8] | $(4.6 \times 10^4)$ | $(1.2 \times 10^5)$ |
| I-5 | 262(25.0), 322(12.3), 341(8.0) | (450, 476, 502); [441, 471, 496, 535] | (56) | (4.5); [20.6] | $(1.2 \times 10^5)$ | $(9.7 \times 10^4)$ |
| I-6 | 273(18.2), 317(13.4), 343(7.4) | (453, 479, 506) [445, 476, 501, 538] | (13) | (0.53); [18.9] | $(2.4 \times 10^5)$ | $(1.6 \times 10^6)$ |
| I-7 | 311(9.6), 342(3.2) | (447, 474, 498) [440, 468, 496, 534] | (38) | (7.4); [42.8] | $(5.1 \times 10^4)$ | $(8.4 \times 10^4)$ |

In Table 1, $k_r$ and $k_{nr}$ were calculated according to the equations, $k_r = \Phi/\tau_{obs}$ and $k_{nr} = (1/\tau obs) - k_r$; absorption data were recorded in $CH_2Cl_2$ solution; and PL data measured in solid film at RT and in $CH_2Cl_2$ matrix at 77K are depicted in parentheses and square bracket, respectively. (Unless Complexes I-1 and I-2 were recorded in $CH_2Cl_2$ solution)

Figure 7:
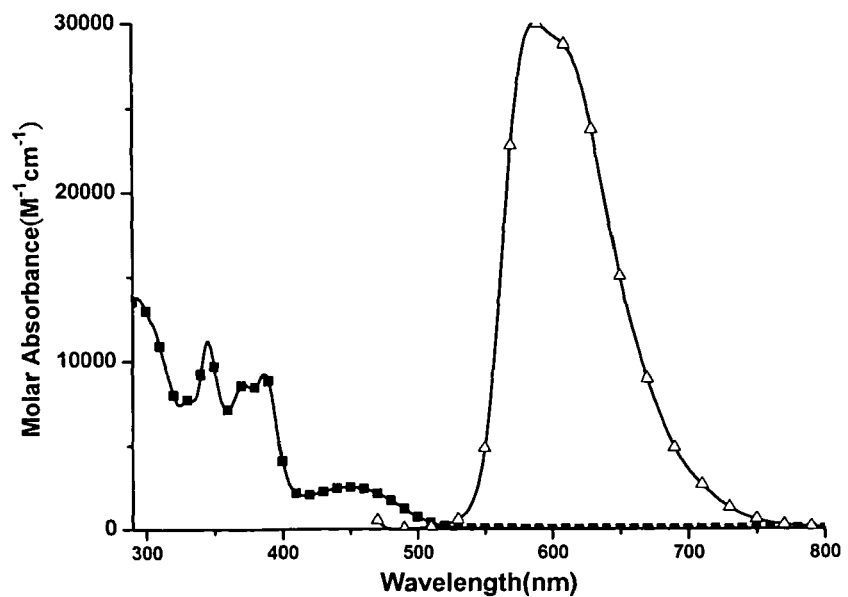
FIG. 7 shows the UV-Vis absorption (in CH$_2$Cl$_2$ solution at room temperature, -■-) and emission spectra (in CH$_2$Cl$_2$ solution at room temperature, -Δ-) of Pt complex (I-1).
Figure 8:
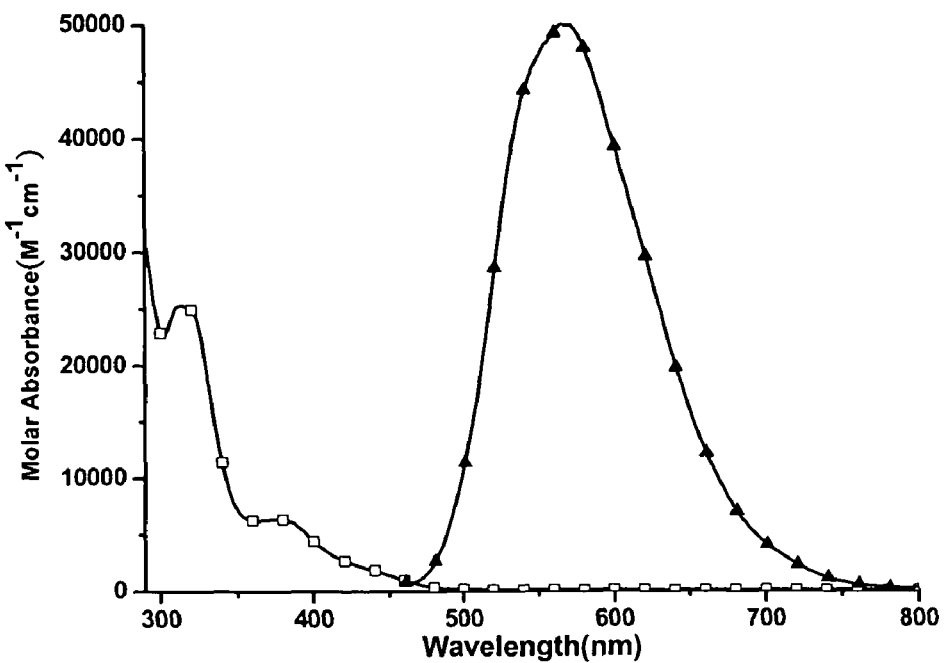
FIG. 8 shows the UV-Vis absorption (in CH$_2$Cl$_2$ solution at room temperature, -□-) and emission spectra (in CH$_2$Cl$_2$ solution at room temperature, -▲-) of Pt complex (I-2).
Figure 9:
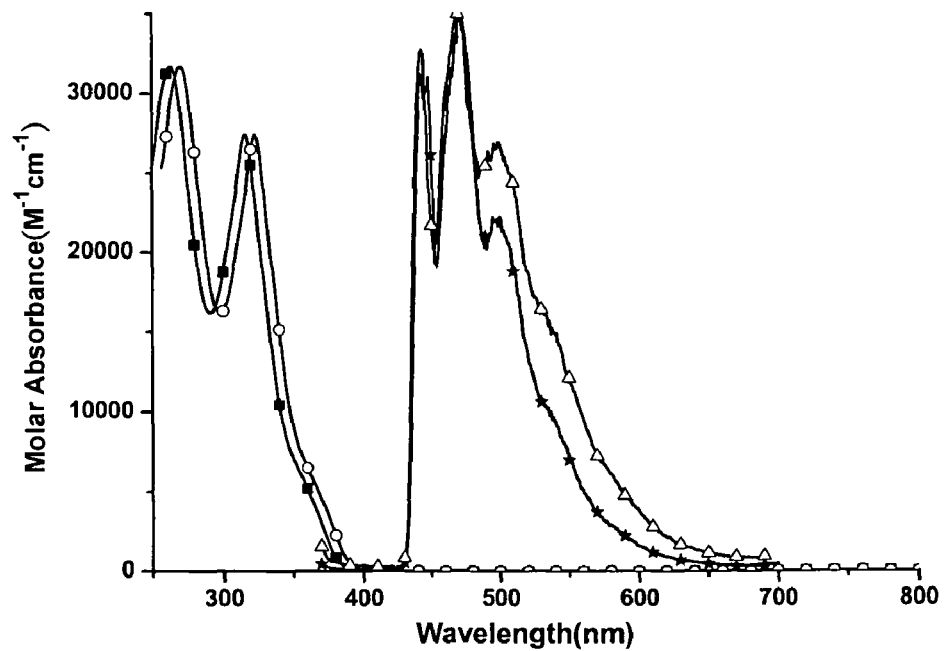
FIG. 9 shows the UV-Vis absorption (in CH$_2$Cl$_2$ solution at room temperature, -■- for Pt complex (I-3), -○- for Pt complex (I-4)) and emission spectra (in frozen CH$_2$Cl$_2$ matrices at 77K, -★- for Pt complex (I-3), -Δ- for Pt complex (I-4)) of Pt complexes (I-3) and (I-4).
Figure 10:
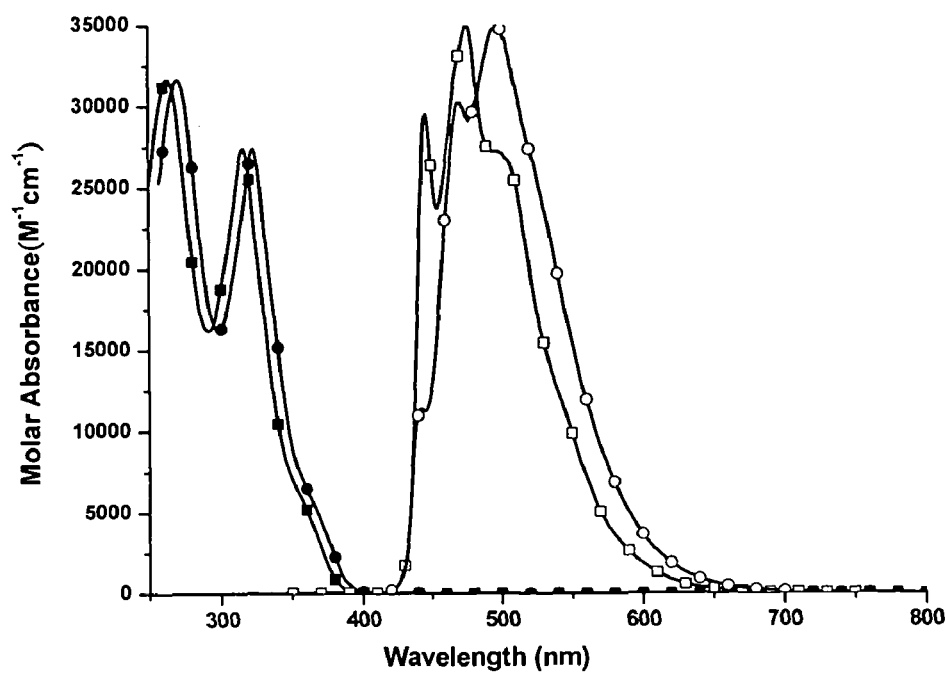
FIG. 10 shows the UV-Vis absorption (in CH$_2$Cl$_2$ solution at room temperature, -■- for Pt complex (I-3), -●- for Pt complex (I-4)) and emission spectra (in film at room temperature, -□- for Pt complex (I-3), -○- for Pt complex (I-4)) of Pt complexes (I-3) and (I-4).
Figure 11:
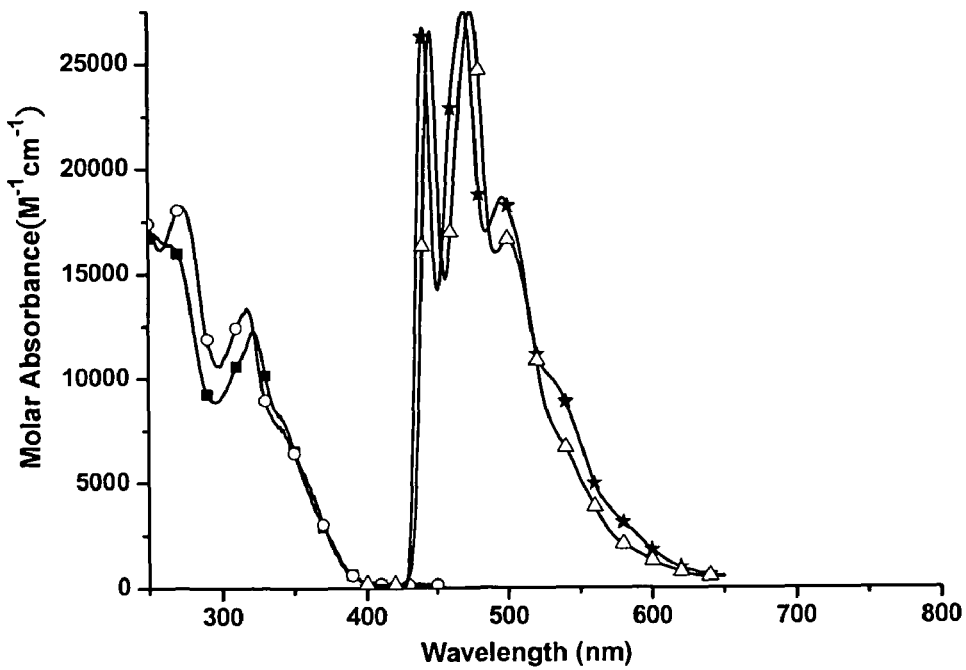
FIG. 11 shows the UV-Vis absorption (in CH$_2$Cl$_2$ solution at room temperature, -■- for Pt complex (I-5), -○- for Pt complex (I-6)) and emission spectra (in frozen CH$_2$Cl$_2$ matrices at 77K, -★- for Pt complex (I-5), -Δ- for Pt complex (I-6)) of Pt complexes (I-5) and (I-6).
Figure 12:
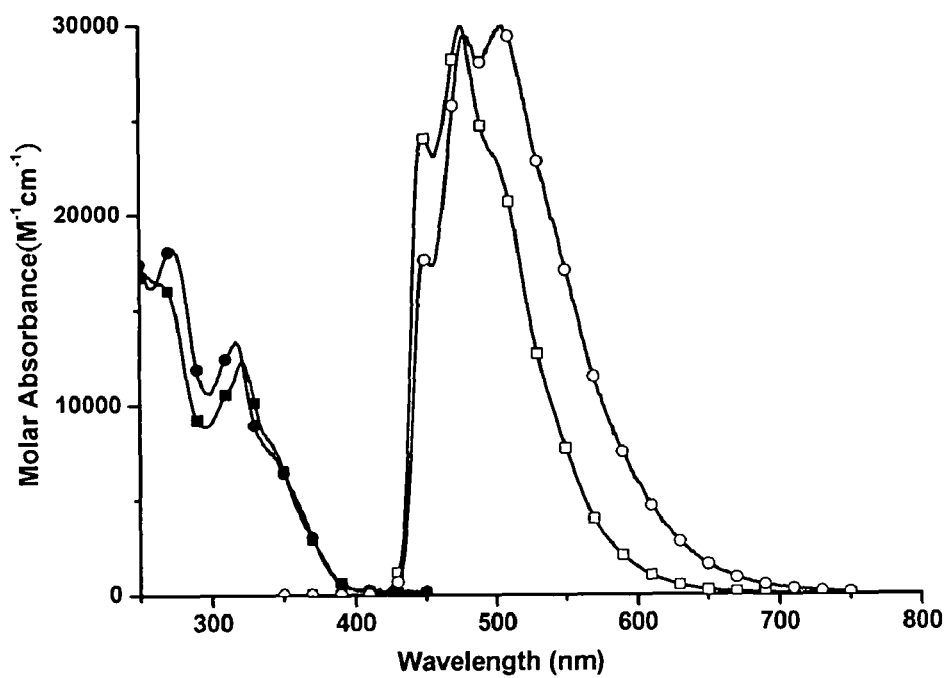
FIG. 12 shows the UV-Vis absorption (in CH$_2$Cl$_2$ solution at room temperature, -■- for Pt complex (I-5), -●- for Pt complex (I-6)) and emission spectra (in film at room temperature, -□- for Pt complex (I-5), -○- for Pt complex (I-6)) of Pt complexes (I-5) and (I-6).
Figure 13:
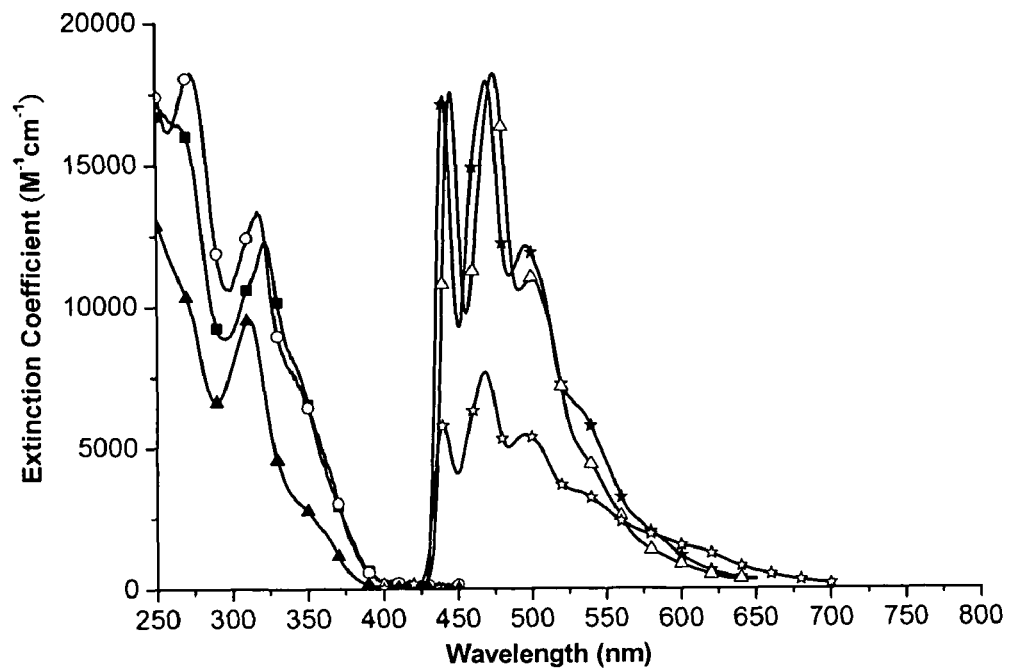
FIG. 13 shows the UV-Vis absorption (in CH$_2$Cl$_2$ solution at room temperature, -■- for Pt complex (I-5), -●- for Pt complex (I-6), -▲- for Pt complex (I-7)) and emission spectra (in frozen CH$_2$Cl$_2$ matrices at 77K, -★- for Pt complex (I-5), -▲- for Pt complex (I-6), -☆- for Pt complex (I-7)) of Pt complexes (I-5), (I-6) and (I-7).

The absorption and luminescence spectra recorded for platinum complexes (I-1) and (I-2) in $CH_2Cl_2$ are depicted in FIGS. 7 and 8, while pertinent data are listed in Table 1. Several remarks can be pointed out from the corresponding spectroscopic and dynamic measurements. As shown in the absorption spectra, the first transition band for the platinum complexes (I-1) and (I-2) were located at ~450 nm and 434 nm, respectively. The results can be rationalized by the $S_0 \to S_1$ transition for the platinum complexes (I-1) and (I-2) being mainly ascribed to the metal-to-ligand charge transfer transition (MLCT) mixed with the intra-ligand charge transfer transition (ILCT) from indazole to isoquinoline moieties, namely 1-iqdz for the platinum complex (I-1) and 3-iqdz for the platinum complex (I-2), respectively.

In addition, the $S_0 \to S_1$ transition for the platinum complex (I-1) tends to be red shifted with respect to that of the platinum complex (I-2) under the same iqdz ligands. For example, the $S_0 \to S_1$ peak wavelength for the platinum complex (I-1) of 450 nm is bathochromic shift by 16 nm compared to the platinum complex (I-2) of 434 nm (see Table 1). The result can be tentatively rationalized by the more facile π-electron delocalization in the case of 1-iqdz (the platinum complex (I-1)), lowering the π* energy and hence a smaller energy gap of the mixed MLCT($d_\pi \to \pi^*$)/ILCT($\pi \to \pi^*$) transition.

As for the emission shown in FIGS. 7 and 8, for the platinum complexes (I-1) and (I-2) studied, the origin of phosphorescence is unambiguous due to its significant $O_2$ quenching as well as the rather long emission lifetime of microseconds (see Table 1). In a good correlation with the trend of absorption spectra, the emission peak wavelength of the platinum complex (I-1) revealed red shift with respect to that of the platinum complex (I-2) bearing the same iqdz ligands (see FIGS. 7-8 and Table 1). More interestingly, in the room temperature, degassed $CH_2Cl_2$ solution, the platinum complex (I-1) exhibit more intense emission yield as compared to that of the platinum complex (I-2). With emission quantum yield and observed lifetime provided, both radiative and nonradiative decay rates can be deduced and the values are listed in Table 1. While the deduced radiative decay rates, $k_{nr}$ for the platinum complex (I-2) ($1.1 \times 10^6$ $s^{-1}$, see Table 1) is larger than that of the platinum complex (I-1) ($4.4 \times 10^4$ $s^{-1}$) by 25 folds. An equally interesting remark is in that the radiative decay rate for the platinum complex (I-1) is calculated to be larger than that for the platinum complex (I-2) by nearly 2 fold. In comparison to the platinum complex (I-2), the increase (decrease) of the radiative (nonradiative) decay rate leads to a significant increase of the emission quantum efficiency for the platinum complex (I-1).

Theoretically, the larger radiative decay rate corresponds to more allowed $S_0$-$T_1$ transition. Based on the first order approximation, it also implies the enhancement of spin-orbit coupling integral, most likely from the more $d_\pi$ contribution of the core heavy metal atom Pt(II). In other words, comparing with the platinum complex (I-2), the experimental results render a proposal of more MLCT contribution for the platinum complex (I-1) in the $T_1$ manifold.

As the platinum complexes (I-1) and (I-2), the dinuclear pyrazolate-bridge complexes (I-3) to (I-6) and the mononuclear complex (I-7) also exhibit enhanced emission quantum yields and short phosphorescence radiative lifetimes in the range of several microseconds, resulting from the steric hinderance preventing stacking behavior of the platinum complexes. In addition, the platinum complexes (I-3) to (I-7) bear fppz ligands leading blue emission.

As for the absorption shown in FIGS. 9 to 12, for the platinum complexes (I-3) to (I-6) studied, the high energy absorption bands at ~320 nm of the platinum complexes (I-3) to (I-6) can be reasonably assigned to the azolate→pyridine intra-ligand $\pi\pi^*$ transition, which is also identified by their large extinction coefficients of $1.2 \sim 2.4 \times 10^4$ $M^{-1}$ $cm^{-1}$. The next lower energy band with the peak wavelength at ~350 nm is assigned to the spin allowed [1]MLCT transition due to its relatively lower extinction coefficient of $<7 \times 10^3$ $M^{-1}$ $cm^{-1}$.

Moreover, in comparison to the mononuclear complex (I-7) (see FIG. 13), the lower lying absorption of dinuclear complexes (I-5) (or complexes (I-6)) is slightly red-shifted in peak wavelength and the associated extinction coefficient is approximately twice larger. These results suggested that the electronic transitions character of dinuclear complexes (I-5) (or complexes (I-6)) can be qualitatively divided into two structural segments resemble that of (I-7), and the Pt—Pt interaction in the dinuclear complexes should be responsible for the observed small difference in energy gaps.

We unfortunately could not resolve any emission for all isomeric platinum complexes of (I-3) to (I-6) in the degassed $CH_2Cl_2$ solution at room temperature. Taking account of the sensitivity of current detecting system, the emission yield, if there is any, is concluded to be less than $10^{-4}$. Such an observation is similar to many Pt(II) complexes which are emissive in the solid state at RT and as glassy solution at lower temperature, whereas they are totally non-emissive in fluid solutions at RT. Perhaps, the quenching processes associated with e.g. solvent collision and/or large amplitude motions can be drastically reduced by freezing solvent molecules in the cryogenic temperature or in a form of solid film. Evidence of this is provided by the strong emission acquired in the 77 K $CH_2Cl_2$ matrix as well as in the room temperature solid film for both platinum complexes (I-3) to (I-6) (see FIGS. 9 to 12). In solid film, the deduced radiative lifetime of <25 μs for all isomers ensures the origin of emission from the triplet manifold, i.e. the phosphorescence. The short radiative lifetime, in combination with the feature of vibronic progression in emission spectra, manifests the $T_1$-$S_0$ transition to be with ligand $\pi\pi^*$ properties mixed, in part, with the metal-to-ligand charge transfer character.

One remarkable feature revealed in FIGS. 9 to 12 lies in the emission spectral similarity between solid film and 77 K $CH_2Cl_2$ matrix in terms of peak wavelength and vibronic progression, except the changes of intensity ratio among the vibronic peaks. Upon quickly plunging the sample (being diluted in $CH_2Cl_2$) into the liquid nitrogen environment, the platnium complexes (I-3) to (I-6) should exist in a well dispersed, monomeric form. It is thus reasonable to conclude negligible intermolecular Pt—Pt interaction for the platinum complexes (I-3) to (I-6). Knowing such interaction frequently takes place in Pt(II) complexes, the negligible Pt(II) packing interaction in solid film for the platinum complexes (I-3) to (I-6) can be rationalized by the overall nonplanar structure, in which two Pt(II) units are spatially twisted with respect to each other, avoiding the intermolecular interaction. In a good correlation with the absorption spectra, the phosphorescence peak of the platinum complex (I-3) ($\lambda_{max}$=476 nm) and (I-5) ($\lambda_{max}$=476 nm) in solid film is slightly blue shifted with respect to that of (I-4) ($\lambda_{max}$=478 nm) and (I-6) ($\lambda_{max}$=479 nm). Furthermore, the platinum complexes (I-3) and (I-5) (complex (I-3): Φ=0.55, complex (I-5): Φ=0.56) are in higher emission quantum yield than the platinum complexes (I-4) and (I-6) (complex (I-4): Φ=0.28, complex (I-6): Φ=0.13). The higher emission quantum yield in the platinum complexes (I-3) and (I-5) is mainly due to their smaller nonradiative decay rate, $k_{nr}$. For example, $k_{nr}$ was deduced to be $1.6\times10^6$ s$^{-1}$ for the platinum complexe (I-6), which is larger than that ($9.7\times10^4$ s$^{-1}$) for the platinum complex (I-5) by one order of magnitude.

Accordingly, the present invention provides the complexes (I-1) and (I-2) exhibiting enhanced potential for the application in high efficiency orange OLEDs, and the complexes (I-3) to (I-6) exhibiting enhanced potential for the application in high efficiency blue OLEDs which have been the most difficult to prepare.

(C) OLED Fabrication

Charge transporting materials such as NPB {4,4'-bis[N-(1-naphthyl)-N-phenylamino]biphenyl} and Alq$_3$ [tris(8-hydroxyquinolinato)aluminum (III)], as well as the host material CBP (4,4'-N,N'-dicarbazolyl-1,1'-biphenyl) were synthesized according to literature procedures, [A. Y Sonsale, S. Gopinathan, C. Gopinathan, Indian *J Chem*. 1976, 14, 408; B. E. Koene, D. E. Loy, M. E. Thompson, *Chem. Mater*. 1998, 10, 2235] and were sublimed twice through a temperature-gradient sublimation system before use. BCP (2,9-dimethyl-4,7-diphenyl-1,10-phenanthroline) was obtained from Aldrich. Patterned ITO-coated glass substrates (sheet resistance ≦30 ohms/square) with an effective individual device area of 3.14 mm$^2$ were cleaned by sonication in a detergent solution, water and ethanol, respectively and then dried by a flow of nitrogen. The substrates were further treated with oxygen plasma for 3 min before loading into the vacuum chamber. Various organic layers were deposited sequentially at a rate of 0.1~0.3 nm/s under a pressure of $2\times10^{-5}$ Torr in an Ulvac Cryogenic deposition system. Phosphorescent dopants were co-evaporated with CBP via two independent sources. A thin layer of LiF (1 nm) and a thick layer of Al (150 nm) were followed as the cathode.

DEVICE EXAMPLE 1

Anode: Indium tin oxide (ITO);

Hole transport layer (HTL, 40 nm): 4,4'-bis[N-(1-naphthyl)-N-phenylamino]biphenyl (NPB);

Emissive layer (EML, 30 nm): carbazole biphenyl (CBP) doped with Complex (I-1), with dopant concentration of 6%, 12%, 24%, 50% and 100%;

Hole blocking layer (10 Onm): bathocuproine (BCP);

Electron transport layer (ETL, 30 nm): tris(8-hydroxyquinolinato) aluminium (III) (Alq$_3$);

Cathode: Al (150 nm)/LiF layer (1 nm).

Figure 14:
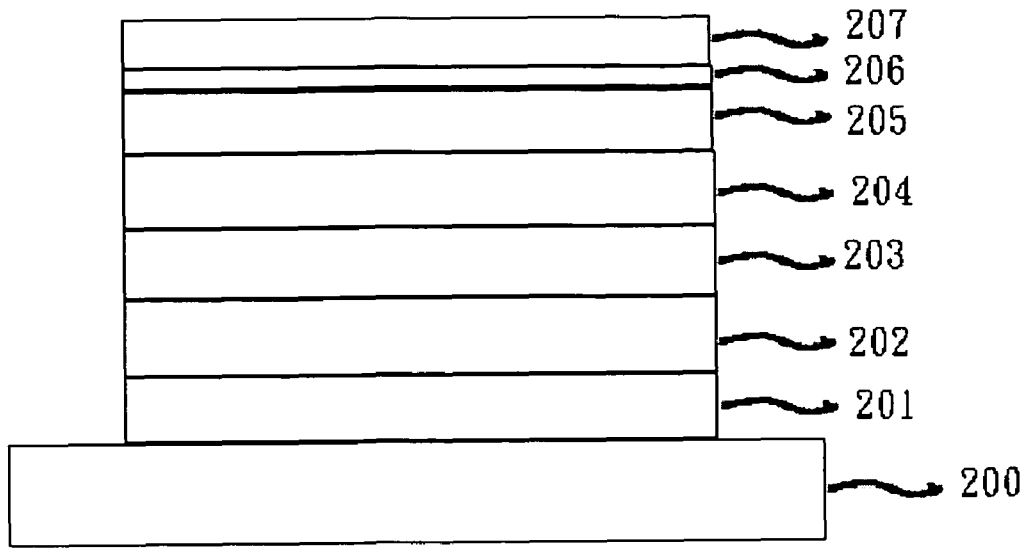
FIG. 14 shows a schematic representation of a phosphorescent OLED according to the present invention.

The schematic representation of a phosphorescent organic light-emitting device of the present invention is shown in FIG. 14. The phosphorescent organic light-emitting device of the present invention comprises a substrate 200 and an anode 201, a hole transport layer 202, an emissive layer 203, a hole blocking layer 204, an electron transport layer 205, a LiF thin layer 206 and a cathode 207 on the surface of the substrate 200 in sequence.

Figure 15:
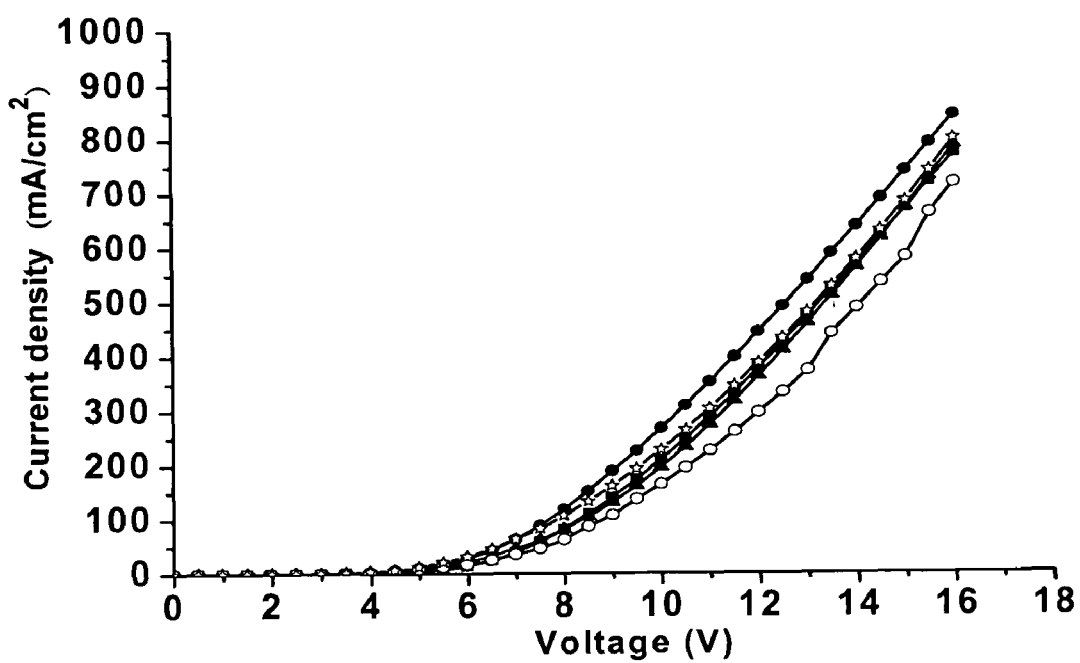
FIG. 15 shows the current-voltage curves of the organic light-emitting devices for Pt complex (I-1) at various doping concentrations (-■- for 6%, -●- for 12%, -▲- for 24%, -○- for 50%, -☆- for 100%).
Figure 16:
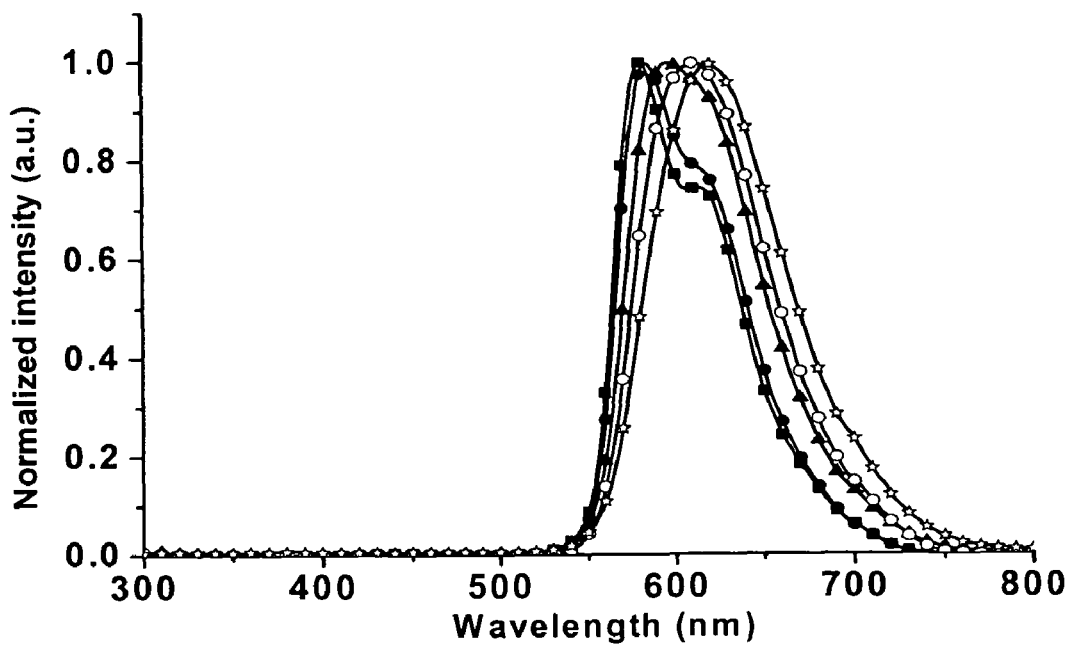
FIG. 16 shows the emission curves of the organic light-emitting devices for Pt complex (I-1) at various doping concentrations (-■- for 6%, -●- for 12%, -▲- for 24%, -○- for 50%, -☆- for 100%).

The crucial device performance characteristics are collected in Table 2, showing the systematic trend that varied according to the five dopant concentrations from 6% to 100%. Orange emission was observed for all the concentrations applied, while the one with a pure layer of the Pt(II) emitter showed the lowest brightness and device efficiencies. FIG. 15 depicts the current-voltage curves of the organic light-emitting devices for Pt complex (I-1) at various doping concentrations, for which the device with 12% of Pt complex (I-1) showed the highest current density compared with all other devices operated under identical voltages. Concomitantly, a small red shifting of the EL emission was observed with increasing dopant concentrations, e.g. from $\lambda_{max}$=581 nm for the 6% device to 618 nm for the device with neat dopant (FIG. 16). This red-shifting effect is presumably attributed to the occurrence of certain degree of intermolecular ππ stacking interaction with increasing the concentration of the planar Pt(II) complex.

Figure 17:
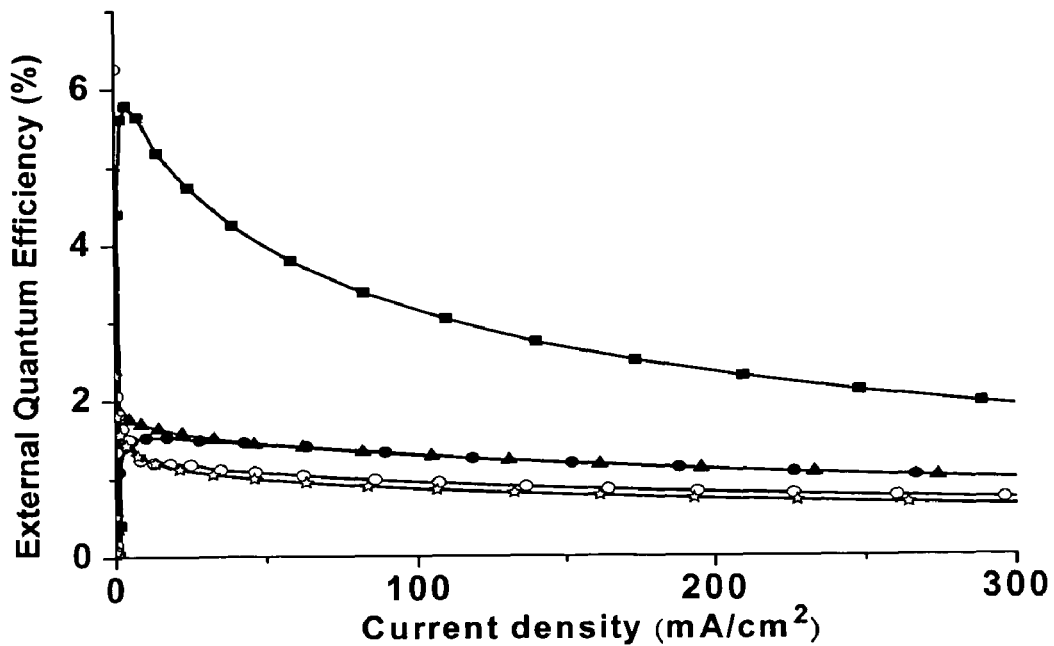
FIG. 17 shows the external quantum efficiency-current curves of the organic light-emitting devices for Pt complex (I-1) at various doping concentrations (-■- for 6%, -●- for 12%, -▲- for 24%, -○- for 50%, -☆- for 100%).

Moreover, among varying the dopant concentrations, the best device performance was achieved at 6 wt % (FIG. 17), which rendered a turn-on voltage of 3 V (at 1 cd/m$^2$) and maximum EQE (external quantum efficiency) of 5.78 at 5 V, gave CIE coordinates of (0.57, 0.43) at 8 V, and reached the maximum brightness of 20296 cd/m² at a driving voltage of 16 V. Like other phosphorescent OLED devices, their efficiencies also witnessed a significantly drop with increasing driving voltage. This can be confirmed by the observation that, at a driving current of 20 mA cm⁻², the external quantum efficiency and luminous efficiency are 4.93% and 12.19 cd A⁻¹, while the efficiencies reduced to 3.16% and 7.82 cd A⁻¹ at 100 mA cm⁻², respectively.

Figure 18:
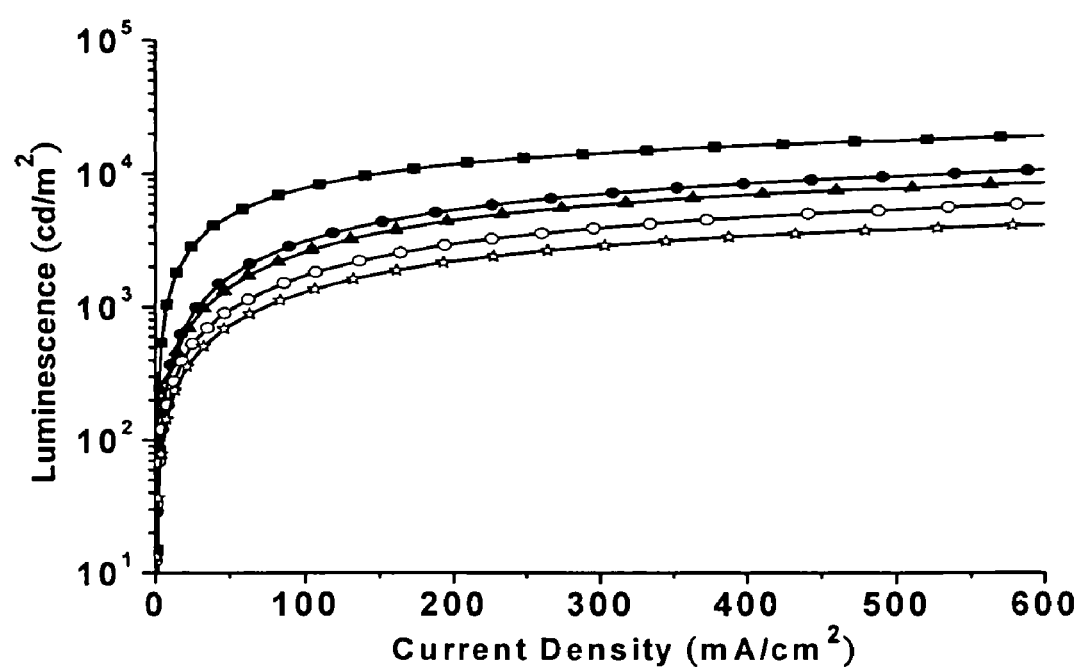
FIG. 18 shows the luminescence brightness-current curves of the organic light-emitting devices for Pt complex (I-1) at various doping concentrations (-■- for 6%, -●- for 12%, -▲- for 24%, -○- for 50%, -☆- for 100%).

Finally, as a result of concentration quenching, raising the doping concentration led to a drastic falloff in device efficiencies. Relatively bright luminescence was also observed for other concentration applied, despite a significant decrease of intensity once the concentration was increased over 6% (FIG. 18), the result of which was evidenced by making a device using 12% of Pt complex (I-1), showing the reduced maximum EQE of only 1.53 at 5.5 V, maximum brightness of 12248 cd/m² at a driving voltage of 16 V and with CIE coordinates of (0.58, 0.42) at 8 V. Upon further increase of the dopant concentration to 100%, the device exhibited a much reduced EQE of 1.14 at 20 mA/cm², while the maximum brightness was lowered to only 4346 cd/m² at 16.0 V and CIE coordinates was measured to be (0.62, 0.37) at 8 V. It is speculated that the lower efficiency at the higher dopant concentration could be due to a combination of two factors, namely the longer emission lifetime of $\tau_{obs}$=8.2 ms and an increasing degree of aggregation despite its possession of a bulky indazolate fragment. The net results may cause the inferiority of the doped devices mainly associated with triplet-triplet annihilation.

that Complex (I-4) was used instead of Complex (I-1). The OLED of the present example emits blue light.

DEVICE EXAMPLE 5

The OLED of the present example was prepared in a similar procedure to that described in Device Example 1 except that Complex (I-5) was used instead of Complex (I-1). The OLED of the present example emits blue light.

DEVICE EXAMPLE 6

The OLED of the present example was prepared in a similar procedure to that described in Device Example 1 except that Complex (I-6) was used instead of Complex (I-1). The OLED of the present example emits blue light.

Although the present invention has been explained in relation to its preferred embodiment, it is to be understood that many other possible modifications and variations can be made without departing from the spirit and scope of the invention as hereinafter claimed.

What is claimed is:
1. A platinum complex of the following formula (I):

TABLE 2

| conc. (%) | Max lum. [cd m⁻² (V)][a] | Quantum eff. [%][b] | Luminous eff. [cd A⁻¹][b] | Power eff. [lm W⁻¹][b] | $\lambda_{max}$ (C.I.E.)[c] |
|---|---|---|---|---|---|
| 6% | 20296 (16.0) | 4.93 (3.16) | 12.19 (7.82) | 6.12 (2.96) | 581, 612 (0.57, 0.43) |
| 12% | 12248 (16.0) | 1.52 (1.30) | 3.64 (3.11) | 2.03 (1.27) | 584, 614 (0.58, 0.42) |
| 24% | 9082 (16.0) | 1.59 (1.29) | 3.17 (2.58) | 1.71 (0.97) | 596, 616 (0.60, 0.40) |
| 50% | 6425 (16.0) | 1.19 (0.95) | 2.14 (1.71) | 1.10 (0.61) | 611 (0.61, 0.38) |
| 100% | 4346 (16.0) | 1.14 (0.86) | 1.70 (1.29) | 0.99 (0.52) | 618 (0.62, 0.37) |

[a]values in the parentheses are the applied driving voltage.
[b]data collected under 20 mA cm⁻², while values in the parentheses are the data collected under 100 mA cm⁻².
[c]measured at the driving voltage of 8 V.

DEVICE EXAMPLE 2

The OLED of the present example was prepared in a similar procedure to that described in Device Example 1 except that Complex (I-2) was used instead of Complex (I-1). The OLED of the present example emits orange light.

DEVICE EXAMPLE 3

The OLED of the present example was prepared in a similar procedure to that described in Device Example 1 except that Complex (I-3) was used instead of Complex (I-1). The OLED of the present example emits blue light.

DEVICE EXAMPLE 4

The OLED of the present example was prepared in a similar procedure to that described in Device Example 1 except

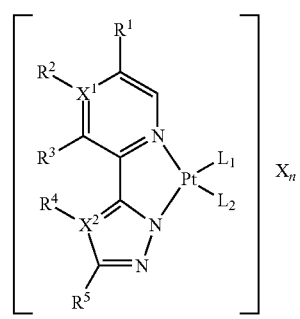

(I)

wherein
X is a counter ion;
n is 0 or 1;

$X^1$ and $X^2$ independently are C or N;

$R^1$, $R^2$ and $R^3$ independently are H, C1-C8 alkyl, phenyl, or C1-C4 perfluoroalkyl, $R^1$ is H and $R^2$ and $R^3$ together are

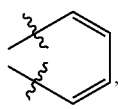, or $R^3$ is H and $R^1$ and $R^2$ together are

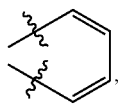, when $X^1$ is C;

$R^1$ and $R^3$ independently are H, C1-C8 alkyl, phenyl, or C1-C4 perfluoroalkyl, and $R^2$ is omitted, when $X^1$ is N;

$R^4$ is H and $R^5$ is H, C1-C8 alkyl, phenyl, or C1-C4 perfluoroalkyl, or $R^4$ and $R^5$ together are C4-C8 alkylene or bridged carbocyclic C4-C12 alkylene, when $X^2$ is C;

$R^4$ is omitted and $R^5$ is H, C1-C8 alkyl, phenyl, or C1-C4 perfluoroalkyl, when $X^2$ is N; and $L^1$ and $L^2$ each are

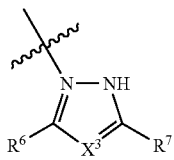

when n is 1, or together are

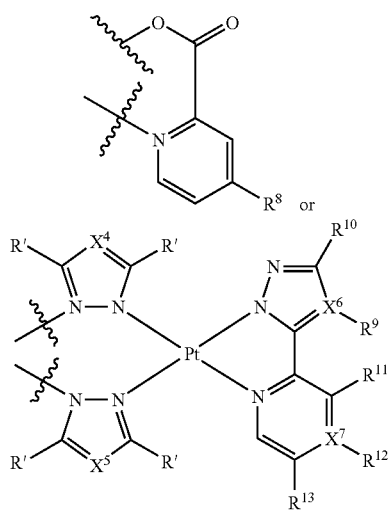

when n is 0, wherein $X^3$ is C or N; $R^6$ and $R^7$ independently are H, C1-C8 alkyl, phenyl, or C1-C4 perfluoroalkyl; $R^8$ is H, C1-C8 alkyl, phenyl, or C1-C4 perfluoroalkyl; $X^4$ and $X^5$ independently are C or N; each R' independently is H, C1-C8 alkyl, phenyl, or C1-C4 perfluoroalkyl; $X^6$ and $X^7$ independently are C or N; $R^9$ is H and $R^{10}$ is H, C1-C8 alkyl, phenyl, or C1-C4 perfluoroalkyl, or $R^9$ and $R^{10}$ together are C4-C8 alkylene or bridged carbocyclic C4-C12 alkylene, when $X^6$ is C; $R^9$ is omitted and $R^{10}$ is H, C1-C8 alkyl, phenyl, or C1-C4 perfluoroalkyl, when $X^6$ is N; $R^{11}$, $R^{12}$ and $R^{13}$ independently are H, C1-C8 alkyl, phenyl, or C1-C4 perfluoroalkyl, $R^{11}$ is H and $R^{12}$ and $R^{13}$ together are

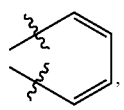, or $R^{13}$ is H and $R^{11}$ and $R^{12}$ together are

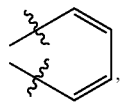, when $X^7$ is C; and $R^{11}$ and $R^{13}$ independently are H, C1-C8 alkyl, phenyl, or C1-C4 perfluoroalkyl and $R^{12}$ is omitted, when $X^7$ is N.

2. The platinum complex as claimed in claim 1, wherein $X^1$, $X^2$, $X^3$, $X^4$, $X^5$, $X^6$ and $X^7$ each are C.

3. The platinum complex as claimed in claim 1, wherein $R^4$ is H and $R^5$ is H, C1-C8 alkyl, phenyl, or C1-C4 perfluoroalkyl, or $R^4$ and $R^5$ together are

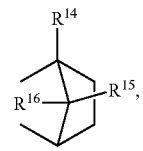

and $R^{14}$, $R^{15}$, and $R^{16}$ independently are C1-8 alkyl.

4. The platinum complex as claimed in claim 3, wherein $R^{14}$, $R^{15}$, and $R^{16}$ each are methyl.

5. The platinum complex as claimed in claim 1, wherein $R^1$, $R^2$ and $R^3$ independently are H, C1-C8 alkyl, phenyl, or C1-C4 perfluoroalkyl; $R^4$ is H; and $R^5$ is H, C1-C8 alkyl, phenyl, or C1-C4 perfluoroalkyl.

6. The platinum complex as claimed in claim 5, wherein $R^5$ is C1-C4 perfluoroalkyl.

7. The platinum complex as claimed in claim 6, wherein $R^5$ is $CF_3$.

8. The platinum complex as claimed in claim 1, wherein $R^1$ is H and $R^2$ and $R^3$ together are

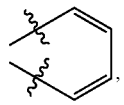, or R³ is H and R¹ and R² together are

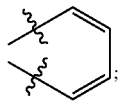

R⁴ and R⁵ together are

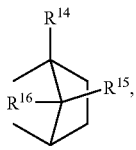

and R¹⁴, R¹⁵, and R¹⁶ independently are C1-8 alkyl.

9. The platinum complex as claimed in claim 1, wherein R⁹ is H and R¹⁰ is H, C1-C8 alkyl, phenyl, or C1-C4 perfluoroalkyl, or R⁹ and R¹⁰ together are

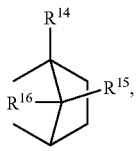

and R¹⁴, R¹⁵, and R¹⁶ independently are C1-8 alkyl.

10. The platinum complex as claimed in claim 9, wherein R¹⁴, R¹⁵, and R¹⁶ each are methyl.

11. The platinum complex as claimed in claim 1, wherein R¹¹, R¹² and R¹³ independently are H, C1-C8 alkyl, phenyl, or C1-C4 perfluoroalkyl; R⁹ is H; and R¹⁰ is H, C1-C8 alkyl, phenyl, or C1-C4 perfluoroalkyl.

12. The platinum complex as claimed in claim 11, wherein R¹⁰ is C1-C4 perfluoroalkyl.

13. The platinum complex as claimed in claim 12, wherein R¹⁰ is CF₃.

14. The platinum complex as claimed in claim 1, wherein R¹¹ is H and R¹² and R¹³ together are

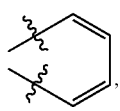

or R¹³ is H and R¹¹ and R¹² together are

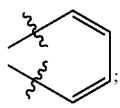

R⁹ and R¹⁰ together are

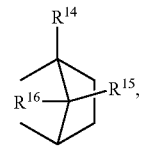

and R¹⁴, R¹⁵, and R¹⁶ independently are C1-8 alkyl.

15. The platinum complex as claimed in claim 1, wherein X¹, X², X³, X⁴, X⁵, X⁶ and X⁷ each are C; R¹, R² and R³ independently are H or C1-8 alkyl, R¹ is H and R² and R³ together are

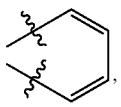

or R³ is H and R¹ and R² together are

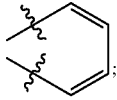

R⁴ is H and R⁵ is C1-C4 perfluoroalkyl, or R⁴ and R⁵ together are

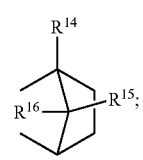

R⁶ and R⁷ each are H or C1-C8 alkyl; R⁸ is H or C1-8 alkyl; each R' independently is H or C1-C8 alkyl; R⁹ is H and R¹⁰ is C1-C4 perfluoroalkyl, or R⁹ and R¹⁰ together are

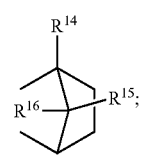

R¹¹, R¹² and R¹³ independently are H or C1-8 alkyl, R¹¹ is H and R¹² and R¹³ together are

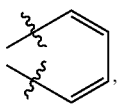

or R$^{13}$ is H and R$^{11}$ and R$^{12}$ together are

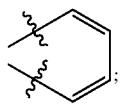

and R$^{14}$, R$^{15}$, and R$^{16}$ are C1-8 alkyl.

16. The platinum complex as claimed in claim 1, wherein the platinum complex is

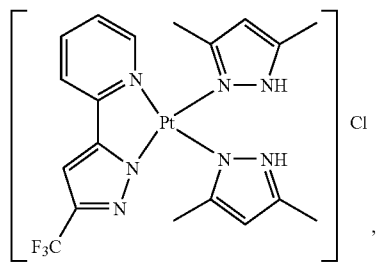

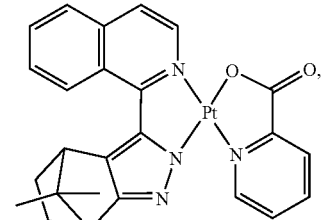

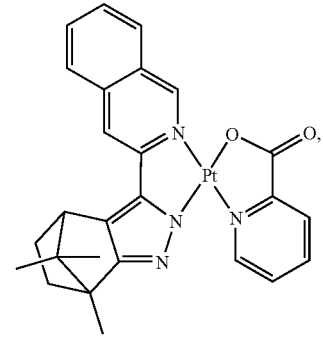

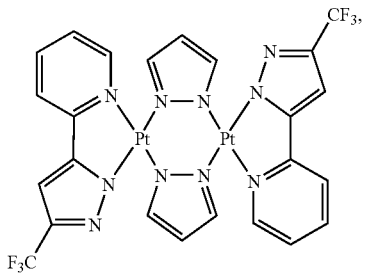

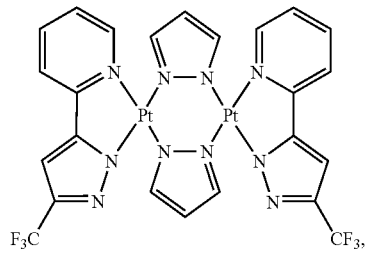

-continued

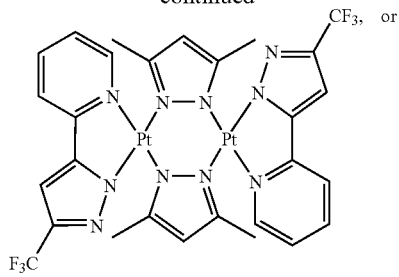

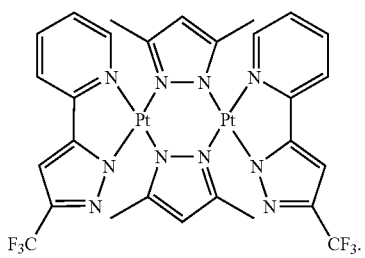

17. An organic light-emitting device, comprising:
an anode;
a cathode; and
one or more organic medium layers including a light-emitting layer disposed between the anode and the cathode,
wherein at least one layer of the organic medium layers comprises a platinum complex of the following formula (I):

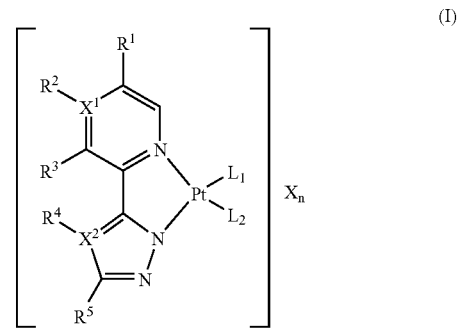

wherein
X is a counter ion;
n is 0 or 1;
X$^1$ and X$^2$ independently are C or N;
R$^1$, R$^2$ and R$^3$ independently are H, C1-C8 alkyl, phenyl, or C1-C4 perfluoroalkyl, R$^1$ is H and R$^2$ and R$^3$ together are

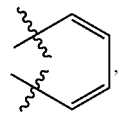

or R$^3$ is H and R$^1$ and R$^2$ together are

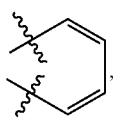

when X$^1$ is C;

R$^1$ and R$^3$ independently are H, C1-C8 alkyl, phenyl, or C1-C4 perfluoroalkyl and R$^2$ is omitted, when X$^1$ is N;

R$^4$ is H and R$^5$ is H, C1-C8 alkyl, phenyl, or C1-C4 perfluoroalkyl, or R$^4$ and R$^5$ together are C4-C8 alkylene or bridged carbocyclic C4-C12 alkylene, when X$^2$ is C;

R$^4$ is omitted and R$^5$ is H, C1-C8 alkyl, phenyl, or C1-C4 perfluoroalkyl, when X$^2$ is N; and L1 and L2 each are

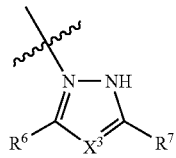

when n is 1, or together are

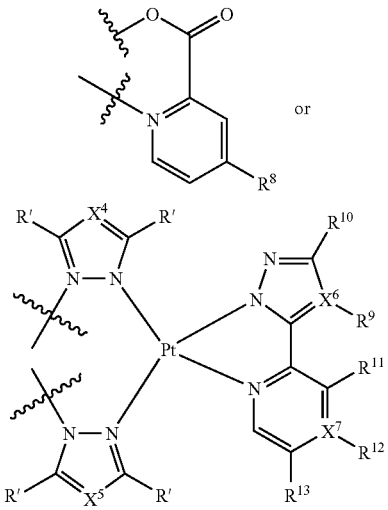

when n is 0, wherein X$^3$ is C or N; R$^6$ and R$^7$ independently are H, C1-C8 alkyl, phenyl, or C1-C4 perfluoroalkyl; R$^8$ is H, C1-C8 alkyl, phenyl, or C1-C4 perfluoroalkyl; X$^4$ and X$^5$ independently are C or N; each R' independently is H, C1-C8 alkyl, phenyl, or C1-C4 perfluoroalkyl; X$^6$ and X$^7$ independently are C or N; R$^9$ is H and R$^{10}$ is H, C1-C8 alkyl, phenyl, or C1-C4 perfluoroalkyl, or R$^9$ and R$^{10}$ together are C4-C8 alkylene or bridged carbocyclic C4-C12 alkylene, when X$^6$ is C; R$^9$ is omitted and R$^{10}$ is H, C1-C8 alkyl, phenyl, or C1-C4 perfluoroalkyl, when X$^6$ is N; R$^{11}$, R$^{12}$ and R$^{13}$ independently are H, C1-C8 alkyl, phenyl, or C1-C4 perfluoroalkyl, R$^{11}$ is H and R$^{12}$ and R$^{13}$ together are

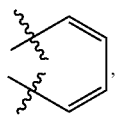

or R$^{13}$ is H and R$^{11}$ and R$^{12}$ together are

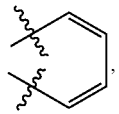

when X$^7$ is C; and R$^{11}$ and R$^{13}$ independently are H, C1-C8 alkyl, phenyl, or C1-C4 perfluoroalkyl and R$^{12}$ is omitted, when X$^7$ is N.

18. The organic light-emitting device as claimed in claim 17, wherein the light-emitting layer is made of at least one host material doped with the platinum complex.

19. The platinum complex as claimed in claim 17, wherein X$^1$, X$^2$, X$^3$, X$^4$, X$^5$, X$^6$ and X$^7$ each are C.

20. The platinum complex as claimed in claim 17, wherein R$^1$, R$^2$ and R$^3$ independently are H, C1-C8 alkyl, phenyl, or C1-C4 perfluoroalkyl; R$^4$ is H; and R$^5$ is H, C1-C8 alkyl, phenyl, or C1-C4 perfluoroalkyl.

21. The platinum complex as claimed in claim 17, wherein R$^1$ is H and R$^2$ and R$^3$ together are

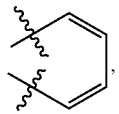

or R$^3$ is H and R$^1$ and R$^2$ together are

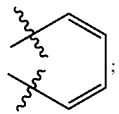

and R$^4$ and R$^5$ together are

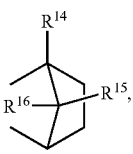

and R$^{14}$, R$^{15}$, and R$^{16}$ independently are C1-8 alkyl.

22. The platinum complex as claimed in claim 17, wherein R$^{11}$, R$^{12}$ and R$^{13}$ independently are H, C1-C8 alkyl, phenyl, or C1-C4 perfluoroalkyl; R$^9$ is H; and R$^{10}$ is H, C1-C8 alkyl, phenyl, or C1-C4 perfluoroalkyl.

23. The platinum complex as claimed in claim 17, wherein $R^{11}$ is H and $R^{12}$ and $R^{13}$ together are

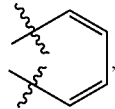

or $R^{13}$ is H and $R^{11}$ and $R^{12}$ together are

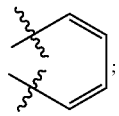

and $R^9$ and $R^{10}$ together are

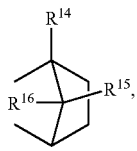

and $R^{14}$, $R^{15}$, and $R^{16}$ independently are C1-8 alkyl.

24. The platinum complex as claimed in claim 17, wherein $X^1$, $X^2$, $X^3$, $X^4$, $X^5$, $X^6$ and $X^7$ each are C; $R^1$, $R^2$ and $R^3$ independently are H or C1-8 alkyl, $R^1$ is H and $R^2$ and $R^3$ together are

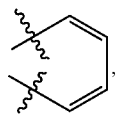

or $R^3$ is H and $R^1$ and $R^2$ together are

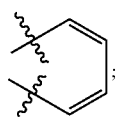

$R^4$ is H and $R^5$ is C1-C4 perfluoroalkyl, or $R^4$ and $R^5$ together are

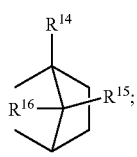

$R^6$ and $R^7$ each are H or C1-C8 alkyl; $R^8$ is H or C1-8 alkyl; each R' independently is H or C1-C8 alkyl; $R^9$ is H and $R^{10}$ is C1-C4 perfluoroalkyl, or $R^9$ and $R^{10}$ together are

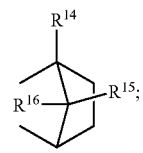

$R^{11}$, $R^{12}$ and $R^{13}$ independently are H or C1-8 alkyl, $R^{11}$ is H and $R^{12}$ and $R^{13}$ together are

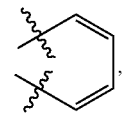

or $R^{13}$ is H and $R^{11}$ and $R^{12}$ together are

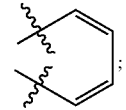

and $R^{14}$, $R^{15}$, and $R^{16}$ are C1-8 alkyl.

25. The organic light-emitting device as claimed in claim 17, wherein the platinum complex is

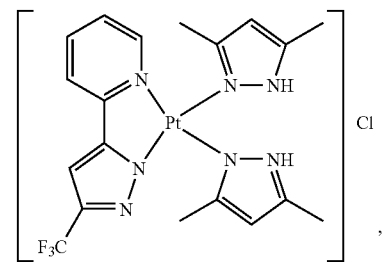

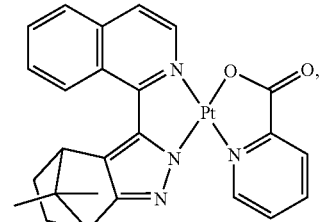

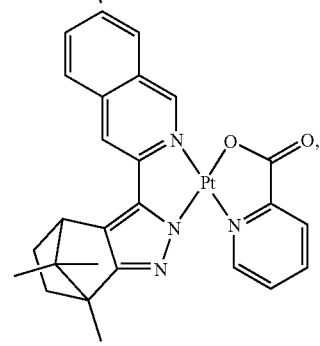

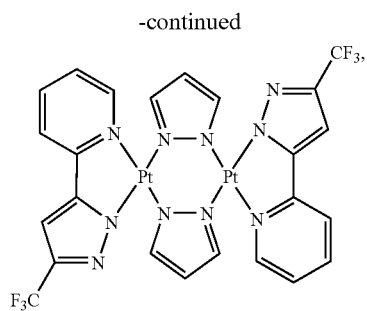
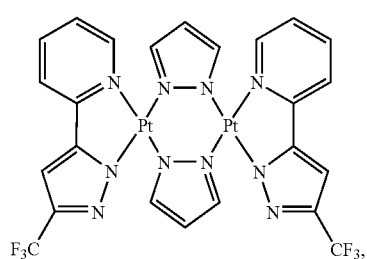
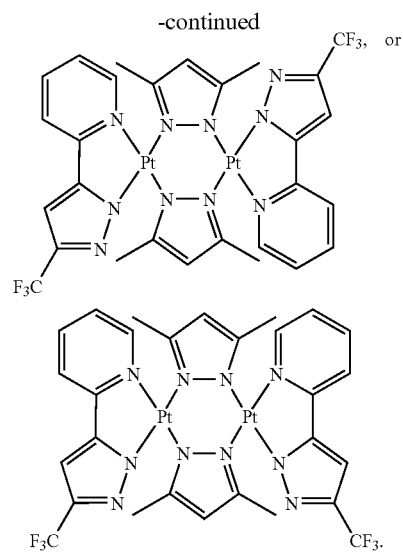
* * * * *